US012601737B2

(12) United States Patent
Kim et al.

(10) Patent No.: US 12,601,737 B2
(45) Date of Patent: Apr. 14, 2026

(54) CONJUGATE FOR IMMUNODETECTION BASED ON LATERAL FLOW ASSAY, AND IMMUNODETECTION METHOD USING SAME

(71) Applicant: GMD BIOTECH, INC., Gwangju (KR)

(72) Inventors: Min Gon Kim, Gwangju (KR); Gyeo Re Han, Gwangju (KR)

(73) Assignee: GMD BIOTECH, INC., Gwangju (KR)

( * ) Notice: Subject to any disclaimer, the term of this patent is extended or adjusted under 35 U.S.C. 154(b) by 932 days.

(21) Appl. No.: 17/548,345

(22) Filed: Dec. 10, 2021

(65) Prior Publication Data

US 2022/0099667 A1 Mar. 31, 2022

Related U.S. Application Data

(63) Continuation of application No. PCT/KR2020/007648, filed on Jun. 12, 2020.

(30) Foreign Application Priority Data

Jun. 12, 2019 (KR) ........................ 10-2019-0069043

(51) Int. Cl.
*G01N 33/53* (2006.01)
*G01N 33/535* (2006.01)
*G01N 33/543* (2006.01)

(52) U.S. Cl.
CPC ... *G01N 33/54388* (2021.08); *G01N 33/5306* (2013.01); *G01N 33/535* (2013.01); *G01N 33/54346* (2013.01)

(58) Field of Classification Search
CPC ............. G01N 33/54388; G01N 33/53; G01N 27/745; G01N 33/54366; C12Q 2549/125; B82Y 30/00
USPC ........................................................ 424/178
See application file for complete search history.

(56) References Cited

FOREIGN PATENT DOCUMENTS

| KR | 10-2012-0083178 A | 7/2012 |
| KR | 10-2018-0110384 A | 10/2018 |
| WO | 2019/032669 A1 | 2/2019 |

OTHER PUBLICATIONS

Kisselev L., Structure, 2002, vol. 10: 8-9.*
Witkowski et al., Biochemistry 38:11643-11650, 1999.*
Whisstock et al., Quarterly Reviews of Biophysics 2003, vol. 36 (3): 307-340.*
Devos et al., Proteins: Structure, Function and Genetics, 2000, vol. 41: 98-107.*
International Search Report issued in PCT/KR2020/007648; mailed Oct. 26, 2020.
Gan, Ning et al.; "An Ultrasensitive Electrochemical Immunosensor for HIV p24 Based on Fe3O4@SiO2 Nanomagnetic Probes and Nanogold Colloid-Labeled Enzyme-Antibody Copolymer as Signal Tag"; Materials (Basel); Mar. 25, 2013; 6(4); pp. 1255-1269; doi:10.3390/ma6041255; PMID: 28809208; PMCID: PMC5452317.
Xiong, Ping et al.; "Incubation-free electrochemical immunoassay for diethylstilbestrol in milk using gold nanoparticle-antibody conjugates for signal amplification"; Microchim Acta; 2014; 181: 453-462; https://doi.org/10.1007/s00604-013-1131-3.

* cited by examiner

*Primary Examiner* — Tekchand Saidha
*Assistant Examiner* — Mohammad Y Meah
(74) *Attorney, Agent, or Firm* — Sughrue Mion, PLLC

(57) ABSTRACT

The present invention relates to a conjugate for immunodetection, an immunodetection sensor including same, and an immunodetection method and an immunodetection signal amplification method using same. Specifically, the present invention has the technical features of: a conjugate for immunodetection based on lateral flow assay, the conjugate including nanoparticles, a polymer conjugated to the nanoparticles and including a plurality of enzymes, and a first binder conjugated to the surface of the polymer and specifically binding to a target specimen; and a use thereof. Accordingly, detection sensitivity is remarkably improved, thereby enabling ultra-high-sensitivity detection, and various antigens and diseases can be simply, quickly, and effectively diagnosed, so that the present invention can be advantageously used.

13 Claims, 13 Drawing Sheets

FIG. 1
① SAMPLE LOADING
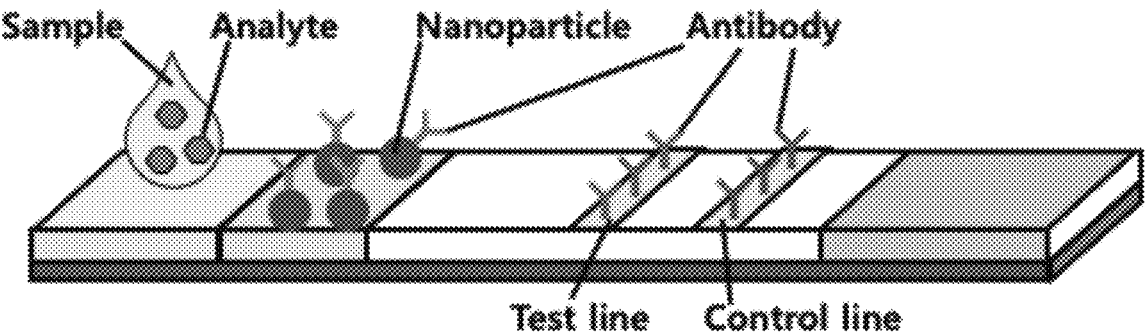
② ANTIGEN-ANTIBODY REACTION
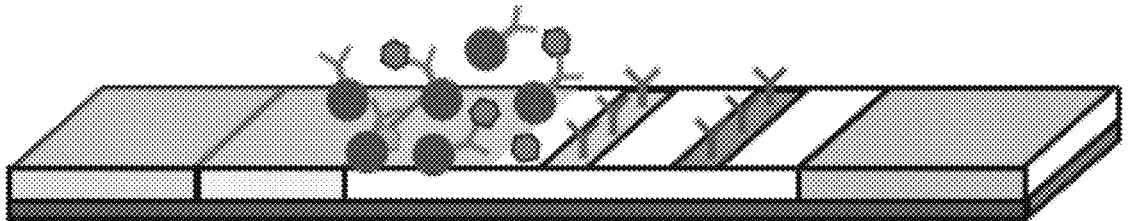
③ COMPLETION AND CONFIRMATION OF REACTION
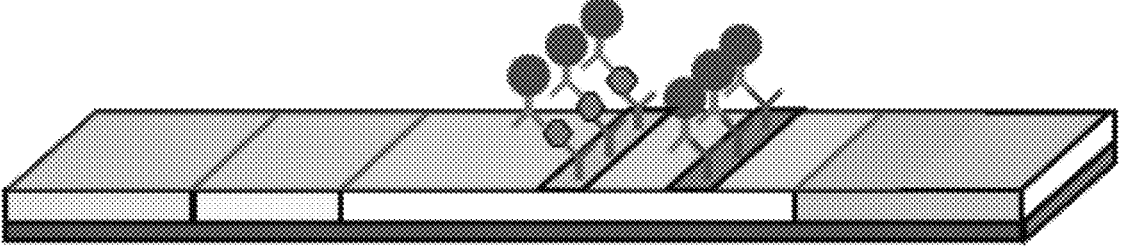

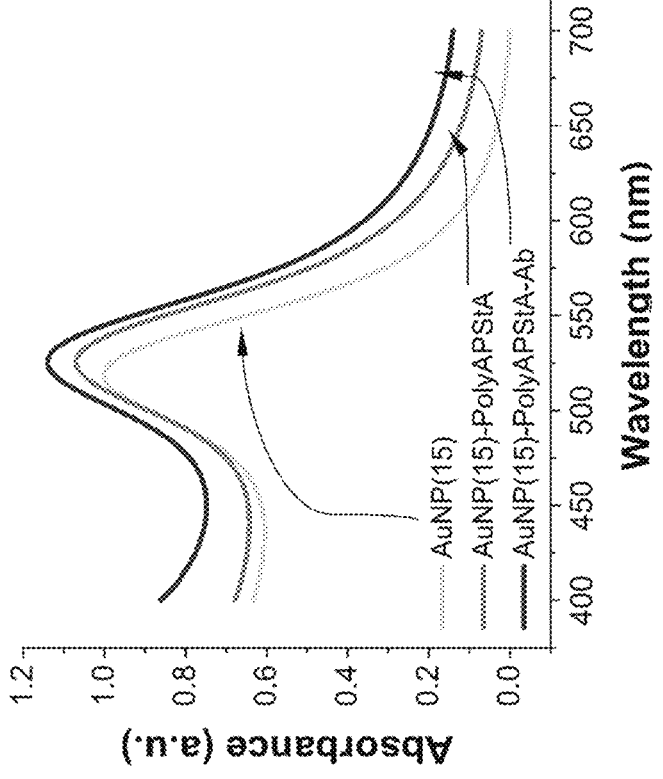
FIG. 3B
Absorbance peak at
15 nm AuNP : 528.7 nm
15nm AuNP-PolyAPStA: 527 nm
15 nm AuNP-PolyAPStA-Antibody: 529 nm
FIG. 3A
Absorbance peak at
15 nm AuNP : 520 nm
15 nm AuNP-PolyHRPStA: 526 nm
15 nm AuNP-PolyHRPStA-Antibody: 528 nm

FIG. 5A          FIG. 5B
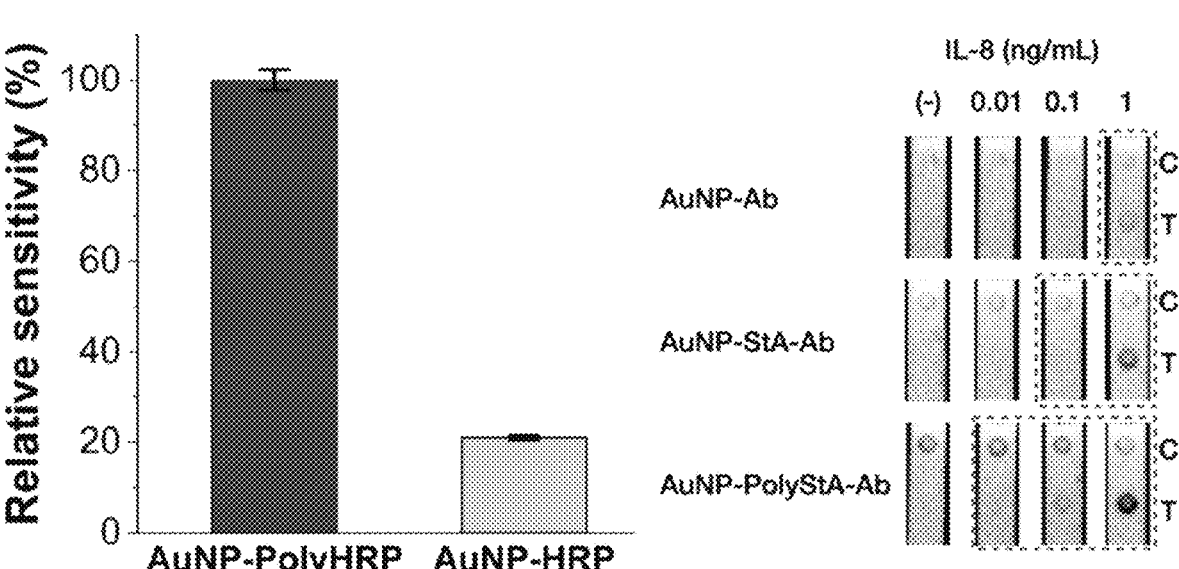
FIG. 5C
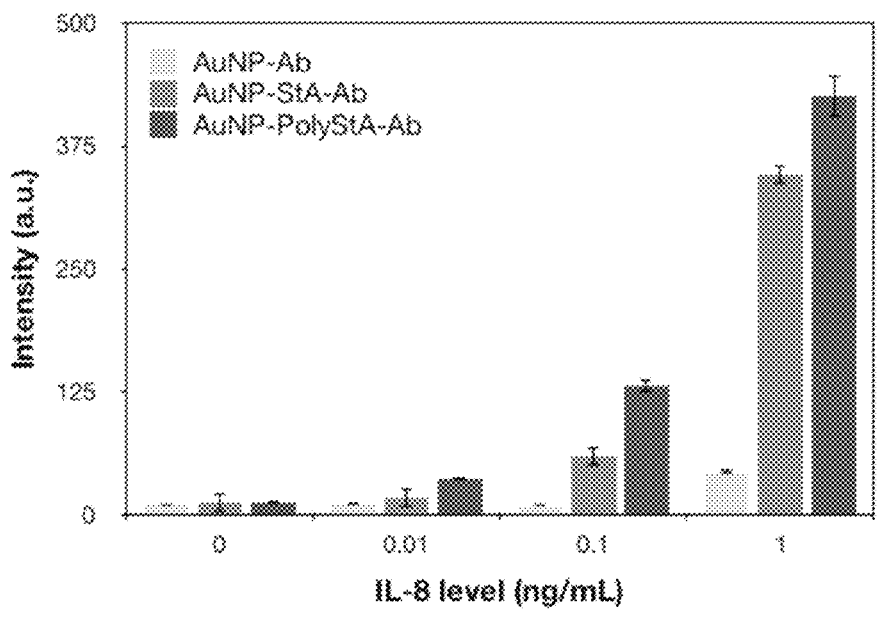

Conjugate Concentration (x)

(a). Colorimetric signal
(BEFORE SIGNAL AMPLIFICATION)

(b). Chemiluminescence (CL) signal
(AFTER SIGNAL AMPLIFICATION)

AuNP-PolyAPStA-Ab conjugate
Conjugate Concentration (x)

(a). Colorimetric signal
(BEFORE SIGNAL AMPLIFICATION)

(b). Colorimetric signal
(AFTER SIGNAL AMPLIFICATION
BY NBT-BCIP REACTION)

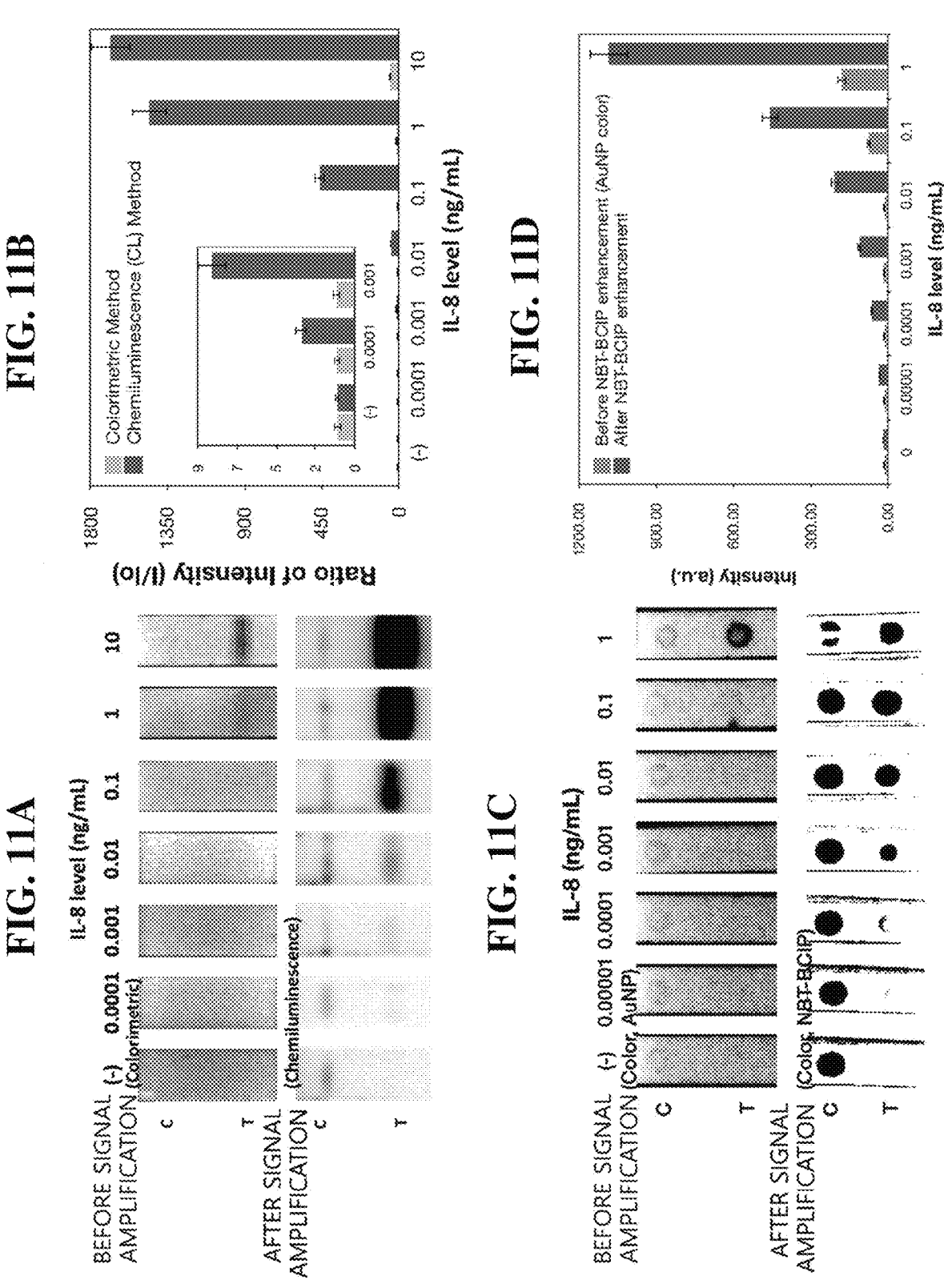

CONJUGATE FOR IMMUNODETECTION BASED ON LATERAL FLOW ASSAY, AND IMMUNODETECTION METHOD USING SAME

CROSS-REFERENCE TO RELATED APPLICATIONS

This application is a Continuation of International Application No. PCT/KR020/007648, filed on Jun. 12, 2020, which claims priority to and the benefit of Korean Patent Application No. 10-2019-0069043, filed on Jun. 12, 2019, the disclosures of which are incorporated herein by reference in its entirety.

TECHNICAL FIELD

The present invention relates to a conjugate for immunodetection based on lateral flow assay, an immunodetection sensor including same, and an immunodetection method and an immunodetection signal amplification method using same, and more particularly, to a conjugate for immunodetection based on lateral flow assay which includes nanoparticles, a polymer conjugated to the nanoparticles and including a plurality of enzymes, and a first binder conjugated to the surface of the polymer and specifically binding to a target analyte.

BACKGROUND ART

A lateral flow assay (LFA) system has been frequently used as a method for rapidly measuring an antibody-antigen response. In the LFA, generally, an antibody is immobilized on a membrane in which a liquid sample may flow in a capillary phenomenon, a conjugate pad and a sample pad are connected to an upper layer of the membrane, and an absorption pad is connected to a lower layer of the membrane. On the conjugate pad, a gold nanoparticle conjugate immobilized with an antibody capable of specifically binding to a sample substance is dried. On the membrane, substances capable of binding to the antibody specifically reacting with the sample substance and the antibody immobilized on the gold nanoparticle are immobilized to different positions, respectively. The antibody immobilized to the membrane and the antibody immobilized to the gold nanoparticle, capable of specifically binding to the sample substance, are configured to bind to the sample substance in a sandwich form. The absorption pad consists of a substance capable of absorbing the liquid sample well. In such an LFA device, when the liquid sample solution is dropped on the sample pad, if the sample is present, the antibody-gold nanoparticle having selectivity and the antibody immobilized to the membrane bind to the sample in a sandwich form to form a band capable of being visibly confirmed on the membrane position immobilized with the antibody. In such a method, since the signal intensity varies according to an antigen concentration, quantification is possible. Generally, since the signal intensity is determined by the color intensity of nanoparticles (ex. AuNP, Latex bead, etc.) immobilized in a test line according to the antigen concentration, mass production is possible and the method has been actively used for disease diagnosis and field diagnosis due to the rapidity and simplicity of the test.

However, a conventional LFA method has a limitation that since the nanoparticle-antibody forms a single conjugate to be signal-detected only in an AuNP color, it is difficult to be applied to antigens required for high-sensitive detection due to low sensitivity (generally, to 1 ng/mL). In order to improve the sensitivity of the LFA, a nanoparticle-antibody-enzyme conjugate has been proposed, and various substrates may be used according to an enzyme type, and as a result, signal amplification by coloring, emission, precipitation reaction, etc. is possible. In addition, as the number of enzymes included in one conjugate is increased, the signal intensity is also increased together, so that antigens at a low concentration can be easily detected.

In order to increase the sensitivity, an enzyme (ex. HRP) in a polymer form has been mainly used for ELISA, Western blotting, Immunohistochemistry, etc. to improve the detection sensitivity of a target protein (Anal. Chem., 2017, 89 (11), pp 6248-6256). As an example, there has been proposed a conjugate of a large multiple molecule or polymer signal body (enzyme polymer) and an antibody (Korean Patent Registration No. 10-1705480). However, there are limitations that a process of fabricating an enzyme polymer-antibody conjugate is complicated and takes a long time, a result analysis method is not clear to deteriorate the reproducibility, and it is difficult to confirm a signal only with a colorless polymer signal body, and as a result, in order to confirm the result, a secondary signal amplification reaction after a primary immune response is required. In addition, there has been proposed a nanoparticle conjugate adsorbed with an enzyme (Biosensors and Bioelectronics 40 (2013) 412-416, Biosensors and Bioelectronics 26 (2011) 2018-2024), but a space where an enzyme can be attached to the surface of the nanoparticle is limited and as a result, there is a limitation to improve the detection sensitivity. Since the conjugation is designed by a method of attaching an enzyme to a remaining space after conjugating a nanoparticle using an antibody or DNA in a form of binding to the enzyme or attaching a biomaterial such as an antibody or DNA to the AuNP surface, the number of enzymes capable of being included per nanoparticle is very limited. In the case of directly conjugating a bioreceptor (antibody or DNA) binding to a target substance to the nanoparticle, since the bioreceptor is adsorbed without orientation, there is a limitation that an active site binding to the target substance is not exposed to the outside and bound and thus, may not easily bind to the target substance.

Therefore, there is still the demand for an immunodetection sensor based on lateral flow assay capable of diagnosing or detecting a trace of analyte in a sample with high accuracy and low cost while solving a technical limitation of a conventional known method.

DISCLOSURE

Technical Problem

The present invention has been made in an effort to provide an immunodetection sensor based on lateral flow assay capable of diagnosing or detecting a trace of analyte in a sample with high accuracy and low cost while solving a technical limitation of a conventional known method and an immunodetection method capable of effectively detecting an antigen.

Technical Solution

According to an exemplary embodiment of the present invention, there is provided a conjugate for immunodetection based on lateral flow assay including nanoparticles, a polymer conjugated or binding to the nanoparticles and including a plurality of enzymes, and a first binder conjugated or binding to the surface of the polymer and specifically conjugated or binding to a target analyte.

According to another exemplary embodiment of the present invention, there is provided an immunodetection sensor based on lateral flow assay including the conjugate for immunodetection based on lateral flow assay.

According to yet another exemplary embodiment of the present invention, there is provided an immunodetection sensor based on lateral flow assay including (i) an absorptive sample pad, (ii) a conjugate pad including a conjugate for immunodetection including nanoparticles, a polymer conjugated to the nanoparticles and including a plurality of enzymes, and a first binder conjugated to the surface of the polymer and specifically binding to a target analyte, (iii) a detection area made of a porous membrane including a test line where a second binder specifically binding to the target analyte bound with the first binder of the conjugate is immobilized and a control line where a third binder specifically binding to the first binder without specifically binding to the target analyte is immobilized, and (iv) an adsorption pad, which are disposed sequentially toward the other end from one end.

According to yet another exemplary embodiment of the present invention, there is provided an immunodetection method based on lateral flow assay including: mixing a sample with the conjugate for immunodetection based on lateral flow assay to specifically bind the conjugate to a target analyte in the sample.

According to yet another exemplary embodiment of the present invention, there is provided an immunodetection signal amplification method comprising: mixing a sample with the conjugate for immunodetection based on lateral flow assay to specifically bind the conjugate to a target analyte in the sample.

According to yet another exemplary embodiment of the present invention, there is provided a method for manufacturing any one conjugate for immunodetection based on lateral flow assay described above including: S1) conjugating nanoparticles and a polymer including a plurality of enzymes; and S2) conjugating a first binder specifically binding to a target analyte to the polymer in the nanoparticle-polymer conjugate.

Advantageous Effects

According to the present invention, in the conjugate for immunodetection and the immunodetection method using the same, since it is possible to improve the detection sensitivity 1000 to 10000 times greater than a conventional antibody for immunodetection, to control whether to use a signal amplification reaction according to a concentration of an antibody to be detected, and to determine whether to detect the antigen, a detection dynamic range is increased and a process of manufacturing the conjugate is simplified and easy. Since the analysis is performed based on typical nanoparticles, the accuracy and reproducibility in the conjugate analysis and quantification process are excellent, a plurality of enzymes and a binding substance (streptavidin) bind to a polymer backbone to significantly increase the number of enzymes capable of being conjugated to individual nanoparticles, thereby enabling the ultra-high sensitive detection and enabling the detection to antigens at a low concentration within a relatively short time as compared with the related art. Since a ratio of binders (antibodies) directly/indirectly binding or conjugated to the nanoparticle surface is higher than a ratio of binders (antibodies) reacting with a target analyte directly attached to the nanoparticle surface, the orientation is improved to have good reactivity to the target substance. Since the conjugate is manufactured around a spherical nanoparticle, the resistance received from the membrane and the pad is lower than a polymer-antibody conjugate structure as a linear polymer structure to have excellent flow efficiency, so that accurate result signal detection is possible due to a low non-specific reaction and a background signal. Therefore, it is possible to simply, rapidly, and effectively diagnose various antigens and diseases.

DESCRIPTION OF DRAWINGS

FIG. 1 is a diagram illustrating an operation principle of a typical membrane-based biosensor.

FIGS. 3A and 3B are diagrams illustrating an absorption spectrum result of a conjugate for immunodetection according to an exemplary embodiment of the present invention.

FIGS. 5A to 5C are diagrams illustrating a result of evaluating the sensitivity of the conjugate for immunodetection according to the exemplary embodiment of the present invention.

FIGS. 8A to 9B are diagrams illustrating a result of evaluating the degree of improving the sensitivity in the case of using the conjugate for immunodetection according to the exemplary embodiment of the present invention.

FIGS. 11A to 11D are diagrams illustrating a detection result of a conjugate (AuNPPolyHRPStA-Interleukin 8 Antibody or AuNP-PolyAPStA-Interleukin 8 Antibody in a sensor) for immunodetection according to an exemplary embodiment of the present invention.

BEST MODE

Figure 2:
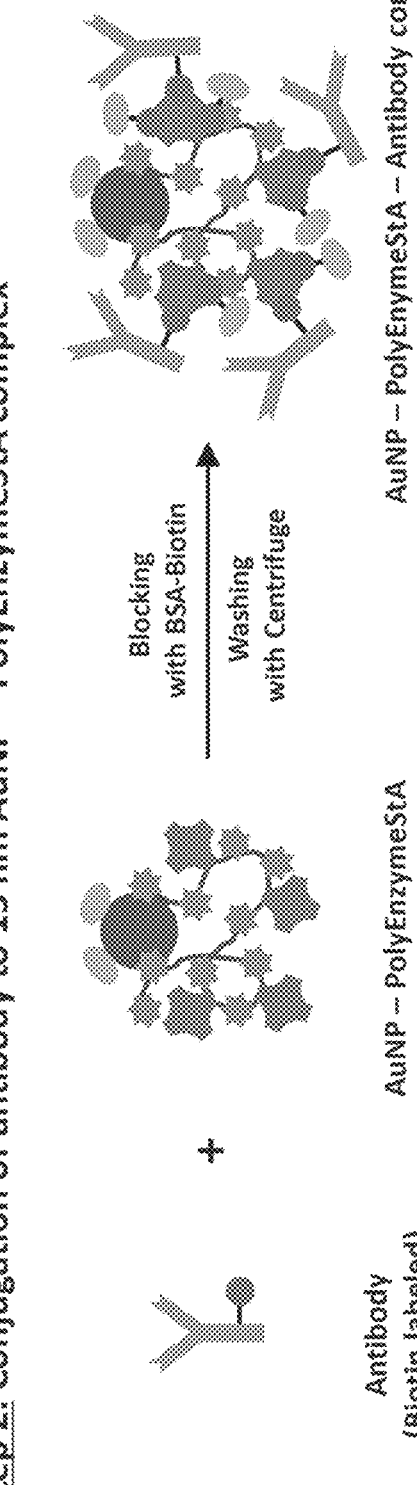
FIG. 2 is a diagram illustrating a process of manufacturing a conjugate for immunodetection according to the present invention.

According to an exemplary embodiment of the present invention, there is provided a conjugate for immunodetection based on lateral flow assay including nanoparticles, a polymer conjugated or binding to the nanoparticles and including a plurality of enzymes, and a first binder conjugated or binding to the surface of the polymer and specifically conjugated or binding to a target analyte.

In the conjugate for immunodetection based on lateral flow assay according to the present invention, the nanoparticles may be at least one selected from the group consisting of metal nanoparticles, quantum dot nanoparticles, magnetic nanoparticles, carbon nanoparticles, latex beads/fluorescent nanoparticles, and cellulose nanoparticles.

In the method for manufacturing the conjugate for immunodetection according to the present invention, a blocker may be immobilized to a portion of the surface of the nanoparticle to which the polymer is not conjugated, wherein the blocker may be at least one selected from bovine serum albumin, egg albumin, skim milk, casein, soybean-fish derived components, polyethylene glycol (PEG), and polyethylene oxide (PEO).

In the conjugate for immunodetection based on lateral flow assay according to the present invention, the polymer may include a first binding substance, the first binder may include a second binding substance, and the first binder may be conjugated or bind to the polymer by inter-binding of the first binding substance and the second binding substance. Here, the relative terms such as first and second are for distinguishing one binding substance from the other binding substance, and do not represent any order between the first binding substance and the second binding substance.

In the conjugate for immunodetection based on lateral flow assay according to the present invention, the first binding substance and the second bonding substance may be at least one selected from the group consisting of an antigen other than a target antigen-antibody pair, a complementary nucleotide chain pair, a pair of an aptamer and a target substance, a pair of peptides binding to each other, and a pair of avidin or streptavidin and biotin.

In conjugate for immunodetection based on lateral flow assay according to the present invention, the enzyme may be at least one selected from horseradish peroxidase, alkaline phosphatase, β-galactosidase, arthromyces ramosus peroxidase, β-lactamase, glucose-6-phosphate dehydrogenase, urease, uricase, superoxide dismutase, luciferase, pyruvate kinase, lactate dehydrogenase, galactose oxidase, acetylcholine-sterase, enterokinase, tyrosinase, and xanthine oxidase.

In the conjugate for immunodetection based on lateral flow assay according to the present invention, the plurality of enzymes bind to the polymer backbone to enable a detection reaction with a plurality of substrates introduced into the space of the polymer, and has advantages of improving 1000 to 10000 times the detection sensitivity, adjusting a signal amplification reaction, and increasing a detectable range.

In the conjugate for immunodetection based on lateral flow assay according to the present invention, the polymer backbone may be at lease one selected from dextran, dextrin, poly(diallyl dimethyl ammonium chloride), poly(vinylamine) hydrochloride, poly(L-lysinehydrobromide), poly(allylamine), poly(acrylamine), poly(allylamine hydrochloride), poly(4-aminostyrene), poly(N-methylvinylamine), poly(ethylene glycol), poly(diallyldimethylammonium chloride), chitosan, polysialic acids, poly(2-ethyl 2-oxazoline), hyaluronic acid, and hydroxyethyl-starch.

In the conjugate for immunodetection based on lateral flow assay according to the present invention, the first binder may be antibodies, antigens, nucleic acids, aptamers, haptens, antigen proteins, DNA, RNA, DNA-binding proteins, RNA-binding proteins or hormone-receptors.

In the conjugate for immunodetection based on lateral flow assay according to the present invention, the target analyte may be at least one selected from the group consisting of autoantibodies, ligands, natural extracts, peptides, proteins, metal ions, synthetic drugs, natural drugs, metabolites, genomes, virus and products by virus, and bacteria and products by bacteria, and may be particularly proteins, more particularly troponin and interleukin.

In the conjugate for immunodetection based on lateral flow assay according to the present invention, the nanoparticles may be gold nanoparticles, the polymer may be a polymer in which a plurality of horseradish peroxidases and streptavidin bind to a dextran polymer backbone, and the first binder may be an antibody conjugated with biotin, wherein the polymer and the first binder may bind to each other by a biotin-streptavidin bond.

According to yet exemplary embodiment of the present invention, the nanoparticles may be gold nanoparticles, the polymer may be a polymer in which a plurality of horseradish peroxidases and streptavidin bind to a dextran polymer backbone, and the first binder may be an antibody conjugated with biotin, wherein the polymer and the first binder may bind to each other by a biotin-streptavidin bond.

According to yet another exemplary embodiment of the present invention, there is provided an immunodetection sensor based on lateral flow assay including any one conjugate for immunodetection based on lateral flow assay described above.

According to yet another exemplary embodiment of the present invention, there is provided an immunodetection sensor based on lateral flow assay including (i) an absorptive sample pad, (ii) a conjugate pad including a conjugate for immunodetection including nanoparticles, a polymer conjugated to the nanoparticles and including a plurality of enzymes, and a first binder conjugated to the surface of the polymer and specifically binding to a target analyte, (iii) a detection area made of a porous membrane including a test line where a second binder specifically binding to the target analyte bound with the first binder of the conjugate is immobilized and a control line where a third binder specifically binding to the first binder without specifically binding to the target analyte is immobilized, and an (iv) adsorption pad, which are disposed sequentially toward the other end from one end.

According to yet another exemplary embodiment of the present invention, there is provided an immunodetection method based on lateral flow assay comprising: mixing a sample with the conjugate for immunodetection based on lateral flow assay described above to specifically bind the conjugate to a target analyte in the sample.

According to yet another exemplary embodiment of the present invention, there is provided an immunodetection signal amplification method comprising: mixing a sample with the conjugate for immunodetection based on lateral flow assay described above to specifically bind the conjugate to a target analyte in the sample.

According to yet another exemplary embodiment of the present invention, there is provided a method for manufacturing any one conjugate for immunodetection based on lateral flow assay described above comprising: S1) conjugating nanoparticles and a polymer including a plurality of enzymes; and S2) conjugating a first binder specifically binding to a target analyte to the polymer in the nanoparticle-polymer conjugate.

The manufacturing method may further include immobilizing a blocker to a portion of the surface of the nanoparticle to which the polymer is not conjugated, after step S1).

In the method for manufacturing the conjugate for immunodetection according to the present invention, the nanoparticles may be at least one selected from the group consisting of metal nanoparticles, quantum dot nanoparticles, magnetic nanoparticles, carbon nanoparticles, latex beads/fluorescent nanoparticles, and cellulose nanoparticles.

In the method for manufacturing the conjugate for immunodetection according to the present invention, a blocker may be immobilized to a portion of the surface of the nanoparticle to which the polymer is not conjugated, wherein the blocker may be at least one selected from bovine serum albumin, egg albumin, skim milk, casein, soybean-fish derived components, polyethylene glycol (PEG), and polyethylene oxide (PEO).

In the method for manufacturing the conjugate for immunodetection according to the present invention, the polymer may include a first binding substance, the first binder may include a second binding substance, and the first binder may be conjugated or bind to the polymer by inter-binding of the first binding substance and the second binding substance. Here, the relative terms such as first and second are for distinguishing one binding substance from the other binding substance, and do not represent any order between the first binding substance and the second binding substance.

In the method for manufacturing the conjugate for immunodetection according to the present invention, the first binding substance and the second bonding substance may be one or more selected from the group consisting of an antigen other than a target antigen-antibody pair, a complementary nucleotide chain pair, a pair of an aptamer and a target substance, a pair of peptides binding to each other, and a pair of avidin or streptavidin and biotin.

In the method for manufacturing the conjugate for immunodetection according to the present invention, the enzyme may be at least one selected from horseradish peroxidase, alkaline phosphatase, $\beta$-galactosidase, arthromyces ramosus peroxidase, $\beta$-lactamase, glucose-6-phosphate dehydrogenase, urease, uricase, superoxide dismutase, luciferase, pyruvate kinase, lactate dehydrogenase, galactose oxidase, acetylcholine-sterase, enterokinase, tyrosinase, and xanthine oxidase.

In the method for manufacturing the conjugate for immunodetection according to the present invention, the plurality of enzymes may bind to the polymer backbone to enable a detection reaction with a plurality of substrates introduced into the space of the polymer, and have advantages of improving 1000 to 10000 times the detection sensitivity, adjusting a signal amplification reaction, and increasing a detectable range.

In the method for manufacturing the conjugate for immunodetection according to the present invention, the polymer backbone may be at least one selected from dextran, dextrin, poly(diallyl dimethyl ammonium chloride), poly(vinylamine) hydrochloride, poly(L-lysinehydrobromide), poly(allylamine), poly(acrylamine), poly(allylamine hydrochloride), poly(4-aminostyrene), poly(N-methylvinylamine), poly(ethylene glycol), poly(diallyldimethylammonium chloride), chitosan, polysialic acids, poly(2-ethyl 2-oxazoline), hyaluronic acid, and hydroxyethyl-starch.

In the method for manufacturing the conjugate for immunodetection according to the present invention, the first binder may be antibodies, antigens, nucleic acids, aptamers, haptens, antigen proteins, DNA, RNA, DNA-binding proteins, RNA-binding proteins or hormone-receptors.

In the method for manufacturing the conjugate for immunodetection according to the present invention, the target analyte may be at least one selected from the group consisting of autoantibodies, ligands, natural extracts, peptides, proteins, metal ions, synthetic drugs, natural drugs, metabolites, genomes, virus and products by virus, and bacteria and products by bacteria, and may be particularly proteins, more particularly troponin and interleukin.

In the method for manufacturing the conjugate for immunodetection according to the present invention, the nanoparticles may be gold nanoparticles, the polymer may be a polymer in which a plurality of horseradish peroxidases and streptavidin bind to a dextran polymer backbone, and the first binder may be an antibody conjugated with biotin, wherein the polymer and the first binder may bind to each other by a biotin-streptavidin bond.

MODES FOR THE INVENTION

In order to achieve the aforementioned objects, the present invention provides a conjugate for immunodetection based on lateral flow assay including nanoparticles, a polymer conjugated to the nanoparticles and including a plurality of enzymes, and a first binder conjugated to the surface of the polymer and specifically binding to a target analyte, immunodetection sensor and method using same, and the like. Hereinafter, the present invention will be described in detail with reference to the drawings.

The terms used herein may be defined as follows.

The "immunodetection sensor" may refer to a device that is manufactured by combining a device that converts an electrochemical change, a thermal energy change, a fluorescence or color change, and the like shown in a reaction between a biological element and a substance to be analyzed into a recognizable signal.

The "binder" may be antibodies, antigens, nucleic acids, aptamers, haptens, antigen proteins, DNA, DNA-binding proteins or hormone-receptors.

The "antigen" may be any substance that may cause a specific immune responses, specifically, may refer to any molecule or molecular group recognizable by at least one antibody. The antigen contains at least one epitope (a specific biochemical unit that can be recognized by an antibody).

The "antibody" may refer to not only a complete polyclonal or monoclonal antibody, but also its fragments (e.g., Fab, Fab', F(ab')2, and Fv), a single chain (ScFv), a diabody, multispecific antibodies formed of antibody fragments, its mutations, fusion proteins including antibody parts, and any other variation array of immunoglobulin molecules including an antibody recognition site having the desired specificity. The antibody may include antibodies corresponding to any category, for example, IgG, IgA, or IgM (or its subclasses), and antibodies that are not included in a specific class.

The expression "specifically binding" means specificity of a binding reagent, for example, an antibody, and may mean preferentially binding to a defined analyte or target substance. The recognizing of the specific analyte or target substance by the binding reagent or antibody in the presence of another potential target may be a feature of the binding. In some exemplary embodiments, the binding reagent that specifically binds to the analyte may avoid binding with other interference portions or portions in a sample to be tested.

The "sample" is not particularly limited as long as it may contain an analyte to be detected. Illustratively, the sample may be a biological sample, for example, a biological fluid or a biological tissue. Examples of the biological fluid may include urine, blood (whole blood), plasma, serum, saliva, semen, stool, sputum, cerebrospinal fluid, tear, mucus, amniotic fluid, etc. The biological tissue is a cluster of cells, and may correspond to connective tissue, epithelial tissue, muscular tissue, neural tissue, etc., as a specific type of set with intracellular substances which typically form one of structural substances of human, animal, plant, bacteria, fungal or viral structures. In addition, examples of the biological tissue may also include organs, tumors, lymph nodes, arteries, and individual cells(s).

It may be understood that the "analyte" means molecules or other substances in a sample to be detected. For example, the analyte may also include antigenic substances, ligands (mono- or polyepitope), haptens, antibodies, and combinations thereof. Specifically, the analyte may include, for example, toxins, organic compounds, proteins, peptides, microorganisms, amino acids, nucleic acids, hormones, steroids, vitamins, drugs, drug intermediates or by-products, bacteria, virus particles, yeast, fungi, protozoa, and metabolites of the substances or antibodies thereof, but is not necessarily limited thereto. However, the analyte may be typically antigens or antibodies. In this regard, examples of the analyte may include ferritin; creatinine kinase MB (CK-MB); digoxin; phenytoin; phenobarbital; carbamazepine; vancomycin; gentamicin; theophylline; valproic acid; quinidine; luteinizing hormone (LH); follicle-stimulating hormone (FSH); estradiol, progesterone; C-reactive protein (CRP); lipocalin; IgE antibody; cytokine; vitamin B2 micro-globlin; glycosylated hemoglobin (Gly.Hb); cortisol; digitoxin; N-acetylprocainamide (NAPA); procainamide; antibodies against rubella such as rubella IgG and rubella IgM, for example, antibodies against toxoplasmosis such as tox (toxo-IgG) and toxoplasmosis IgM; testosterone; salicylate; acetaminophen; hepatitis B surface antigens (HBsAgs); antibodies against hepatitis B core antigens, for example, anti-hepatitis B core antigens IgG and IgM (anti-HBCs); human immunodeficiency virus 1 and 2 (HIV 1 and 2); human T-cell lymphotrophic virus 1 and 2 (HTLV); hepatitis Be antigen (HBeAg); antibody against hepatitis Be antigen (anti-HBe); influenza virus; thyroid stimulating hormone (TSH); thyroxine (T4); total triiodothyronine (total T3); free triiodothyronine (free T3); carcinoembryonic antigen (CEA); lipid protein, cholesterol, and triglycerides; and alpha-fetoprotein (AFP). Drugs of misuse and control substances may include, specifically, amphetamine; methamphetamine; barbiturate, for example, amobarbital, secobarbital, pentobarbital, phenobarbital and barbital; benzodiazepine, for example, librium and valium; cannabinoid, for example, hashish and marijuana; cocaine; fentanyl; LSD; methaqualone; opiates, for example, heroin, morphine, codeine, hydromorphone, hydrocodone, methadone, oxycodone, oxymorphone and opium; phencyclidine; and propoxyphene, but are not limited thereto.

The "conjugate" may widely mean a specific substance and a detectable label conjugated thereto, wherein as the label, gold nanoparticles may be used and may mean a conjugate in which a binder component (specifically, the first binder) is conjugated thereto.

The term "contacting" narrowly means a direct contact between two substances, but widely, may be understood such that any additional component may be interposed as long as a contact between the component and a liquid flow is performed.

The present invention provides a conjugate for immunodetection based on lateral flow assay including nanoparticles, a polymer conjugated to the nanoparticles and including a plurality of enzymes, and a first binder conjugated to the surface of the polymer and specifically binding to a target analyte.

In the conjugate for immunodetection based on lateral flow assay according to the present invention, the nanoparticles may be at least one selected from the group consisting of metal nanoparticles, quantum dot nanoparticles, magnetic nanoparticles, carbon nanoparticles, latex beads/fluorescent nanoparticles, and cellulose nanoparticles.

The shape of the nanoparticle of the present invention is not particularly limited, and the nanoparticle may be at least one selected from the group consisting of spherical particles, strawberry-like or sea urchin-like spherical particles of which various types of nanoparticles are placed on the surface, anisotropic particles, hollow particles, asymmetric particles, and angulated particles. The nanoparticle may have, for example, a nano sphere, a nano-rod, a nanocube, and a plurality of geometrical and non-geological shapes. In particular, in the case of the anisotropic particle or angulated particle such as a rod shape, a triangle, a prism, and a cube, a more reinforced signal may be provided as compared to the spherical particle in the ramen scattering. The shape and size of the nanoparticle may be appropriately controlled for maximizing surface plasmon. The manufacturing method of the various types of nanoparticles described above is known in a large number of documents.

The nanoparticles of the present invention perform a function as a signal generating substance, and the metal nanoparticles may detect antigens through a color change in metal nanoparticles by a selective reaction between the conjugate for immunodetection and the analyte, and may quantitatively analyze a substance to be analyzed by measuring the absorbance, electric conductivity, and the like of the binder of the conjugate for immunodetection specifically binding to the analyte on the membrane. These metal nanoparticles may, for example, gold, silver, copper, palladium, platinum, aluminum, nickel, iron, titanium, and the like, but are not limited thereto.

According to an exemplary embodiment of the present invention, the metal nanoparticles may be gold nanoparticles, and the gold nanoparticle may have a size of 2 nm to 100 nm. The gold nanoparticles may be manufactured by mixing gold ions and a reducing agent, and are also commercially available even from reagent companies such as Sigma.

In the conjugate for immunodetection based on lateral flow assay according to the present invention, a blocker, for example, at least one selected from bovine serum albumin, skim milk, casein, soybean-fish derived components, and polyethylene glycol may be conjugated or bind to a portion of the surface of the nanoparticle to which the polymer is not conjugated. These blockers may be subjected to pre-treatment such as partial modification by heat, acid, or alkali if necessary.

In the conjugate for immunodetection based on lateral flow assay according to the present invention, the polymer may include a first binding substance, the first binder may include a second binding substance, and the first binder may be conjugated or bind to the polymer by inter-binding of the first binding substance and the second binding substance. Here, the relative terms such as first and second are for distinguishing one binding substance from the other binding substance, and do not represent any order between the first binding substance and the second binding substance.

In the conjugate for immunodetection based on lateral flow assay according to the present invention, the first binding substance and the second bonding substance may be at least one selected from the group consisting of an antigen other than a target antigen-antibody pair, a complementary nucleotide chain pair, a pair of an aptamer and a target substance, a pair of peptides binding to each other, and a pair of avidin or streptavidin and biotin.

In the conjugate for immunodetection based on lateral flow assay according to the present invention, the enzyme may be at least one selected from horseradish peroxidase, alkaline phosphatase, β-galactosidase, arthromyces ramosus peroxidase, β-lactamase, glucose-6-phosphate dehydrogenase, urease, uricase, superoxide dismutase, luciferase, pyruvate kinase, lactate dehydrogenase, galactose oxidase, acetylcholine-sterase, enterokinase, tyrosinase, and xanthine oxidase, and preferably, horseradish peroxidase (HRP) and alkaline phosphatase (ALP).

When the HRP enzyme is supplied with tetramethylbezidine (TMB) or diaminobenzidine (DAB) as a substrate and the ALP enzyme is supplied with nitroblue tetrazolium (NBT) as the substrate, the enzyme decomposes the substrate to produce an enzyme product which is a chromogenic substance, and the product may be measured using the absorbance and intensity at a specific wavelength.

The enzyme can be generally detected by catalyzing the chemical modification of a coloring substrate that may be measured using various techniques. For example, the enzyme may catalyze a color change in substrate that may be measured by a spectrophotometer, or change the fluorescence or chemiluminescence of the substrate. The chemiluminescent substrate is electronically excited by the chemical reaction, and then emit light that may be measured (e.g., using a chemiluminescence photometer) or provide energy to a fluorescent receptor.

A plurality of enzyme molecules of the polymer is polymerized through a suitable method. For example, the plurality of enzyme molecules of the polymer are covalently bonded to each other through covalent bonds, for example, a cross-linking agent. For example, the enzyme includes a protein component. For example, the plurality of enzyme molecules of the polymer are covalently bonded to each other through the protein component. For example, the enzyme molecule includes a polysaccharide component. For example, the plurality of enzyme molecules of the polymer are covalently bonded to each other through the polysaccharide component. For example, the plurality of enzyme molecules of the polymer are covalently bonded to each other through the polysaccharide and protein components. For example, the plurality of enzyme molecules of the polymer are non-covalently bonded to each other. For example, the plurality of enzyme molecules of the polymer include multiple enzymes. For example, the plurality of enzyme molecules include enzyme aggregates.

Generally, the polymerization process is performed under conditions for allowing controlled and reproducible formation of polymerase in a pre-selected size. The concentration of the enzyme, the pH of a buffer, the stoichiometry of a free functional group for a crosslinking reagent, the temperature, and the reaction time are all important factors that achieve this adjustable process.

For example, the polymer includes about 5 to about 500 enzyme molecules. For example, the polymer includes at least about 55, 10, 15, 20, 25, 50, 75, 100, 150, 200, or 250 enzyme molecules. For example, the polymer includes about less than 250, 200, 150, 100, 75, 50, 25, 20, 15, 10 or 5 enzyme molecules.

For example, the enzyme molecules of the polymer are covalently bonded to each other through a polymeric cross-linking agent. For example, the enzyme molecules of the polymer are covalently bonded to each other through a crosslinking agent having a length of 0. For example, the enzyme molecules of the polymer are covalently bonded to each other by a linear method. For example, the enzyme molecules of the polymer are covalently bonded to each other by a branched method. For example, the enzyme molecules of the polymer are covalently bonded to each other by mixed linear and branched methods. For example, the enzyme molecules of the polymer are linked to each other by covalent bonds to form a linear structure. For example, the enzyme molecules of the polymer are covalently bonded to each other to form a spherical structure.

For example, the polymer has a molecular weight of about 500 kDa to about 5 mega Dalton (MDA). For example, the polymer has a molecular weight of at least about 500 kDa. For example, the polymer has a molecular weight of about 5 MDa or less. For example, the polymer has a molecular weight of at least about 750 kDa. For example, the polymer has a molecular weight of at least about 1, 2, 3 or 4 MDa.

For example, the polymer including the plurality of enzymes is first formed before being conjugated to the antibody.

In the conjugate for immunodetection based on lateral flow assay according to the present invention, the polymer in which the plurality of enzymes are conjugated or bind to the polymer backbone has advantages of enabling a detection reaction with a plurality of substrates introduced into the space of the polymer, improving 1000 to 10000 times the detection sensitivity, adjusting a signal amplification reaction, and increasing a detectable range. In addition, according to the exemplary embodiment of the present invention, the binding substance may be conjugated or bind to the polymer backbone.

In the conjugate for immunodetection based on lateral flow assay according to the present invention, the polymer backbone may be at least one selected from dextran, dextrin, poly(diallyl dimethyl ammonium chloride), poly(vinylamine) hydrochloride, poly(L-lysinehydrobromide), poly(allylamine), poly(acrylamine), poly(allylamine hydrochloride), poly(4-aminostyrene), poly(N-methylvinylamine), poly(ethylene glycol), poly(diallyldimethylammonium chloride), chitosan, polysialic acids, poly(2-ethyl 2-oxazoline), hyaluronic acid, and hydroxyethyl-starch.

In the conjugate for immunodetection based on lateral flow assay according to the present invention, the first binder may be antibodies, antigens, nucleic acids, aptamers, haptens, antigen proteins, DNA, RNA, DNA-binding proteins, RNA-binding proteins or hormone-receptors, and the first binder may be at least one thereof, and specifically, the first binder may be antibodies.

For example, the antibody is conjugated to the polymer including the plurality of enzymes. For example, at least one antibody is dispersed and bound to the surface of the polymer.

The conjugate for immunodetection based on lateral flow assay according to the present invention includes conjugates to be used in vitro which are linked to an enzyme (enzyme tag) generating a colored product when the antibody is in contact with a secondary binding ligand and/or coloring substrate. Examples of a suitable enzyme include urease, alkaline phosphatase, horseradish peroxidase, and/or glucose oxidase. A preferred secondary binding ligand is biotin and/or avidin and streptavidin compounds.

The first binder and the polymer may be conjugated to each other by a suitable method. For example, the first binder and the polymer may be conjugated to each other through a linking ring, and the linking ring may be a linking ring by physical bonding and chemical bonding through a biological reaction such as biotin-streptavidin, antigen-antibody, nucleotide bond, ligand-binder, and the like, and in this specification, the first binder and the polymer may be referred to as the first binding substance and the second binding substance.

In the conjugate for immunodetection based on lateral flow assay according to the present invention, the first binder, for example, the antibody is conjugated to the first binding substance of the polymer, for example, streptavidin. In the exemplary embodiment, the polymer is conjugated to a specific site of an antibody or a fragment thereof. In the exemplary embodiment, the polymer is conjugated to at least one specific sites of the antibody or the fragment thereof. In the exemplary embodiment, the polymer is conjugated to a random site of the antibody or the fragment thereof. In the exemplary embodiment, the polymer is conjugated to at least one random sites of the antibody or the fragment thereof. In the exemplary embodiment, the polymer is conjugated to an antibody or a fragment thereof through intrinsic or extrinsic chemical properties of amino acids. In the exemplary embodiment, the polymer is conjugated to an antibody or a fragment thereof through intrinsic or extrinsic chemical properties of amino acid residues.

In an exemplary embodiment, the conjugate for immunodetection includes at least one antibodies. In an exemplary embodiment, the conjugate for immunodetection includes a plurality of enzyme polymers. In an exemplary embodiment, the conjugate for immunodetection includes a plurality of polymers and each polymer includes almost the same number of enzyme molecules. In an exemplary embodiment, the conjugate for immunodetection includes a plurality of polymers and the plurality of polymers represents distribution in the number of enzyme molecules of each polymer. In an exemplary embodiment, the conjugate for immunodetection includes the plurality of polymers and the plurality of polymers represents a difference in a form of the polymer.

In the conjugate for immunodetection based on lateral flow assay according to the present invention, the target analyte may be at least one selected from the group consisting of autoantibodies, ligands, natural extracts, peptides, proteins, metal ions, synthetic drugs, natural drugs, metabolites, genomes, virus and products by virus, and bacteria and products by bacteria, and may be particularly proteins, more particularly troponin and interleukin.

In the conjugate for immunodetection based on lateral flow assay according to the present invention, the nanoparticles may be gold nanoparticles, the polymer may be a polymer in which a plurality of horseradish peroxidases and streptavidin bind to a dextran polymer backbone, and the first binder may be an antibody conjugated with biotin, wherein the polymer and the first binder may bind to each other by a biotin-streptavidin bond.

In the conjugate for immunodetection based on lateral flow assay according to the present invention, the nanoparticles may be gold nanoparticles, the polymer may be a polymer in which a plurality of horseradish peroxidases and streptavidin bind to a dextran polymer backbone, and the first binder may be an antibody conjugated with biotin, wherein the polymer and the first binder may bind to each other by a biotin-streptavidin bond.

According to another exemplary embodiment of the present invention, there is provided an immunodetection sensor based on lateral flow assay including any one conjugate for immunodetection based on lateral flow assay described above. In this regard, FIG. 1 illustrates a schematic configuration of an immunodetection sensor based on lateral flow assay in an exemplary strip form.

As illustrated in FIG. 1, a typical example of the immunodetection sensor based on lateral flow assay provides an immunodetection sensor based on lateral flow assay including (i) an absorptive sample pad, (ii) a conjugate pad including a conjugate for immunodetection including nanoparticles, a polymer conjugated to the nanoparticles and including a plurality of enzymes, and a first binder conjugated to the surface of the polymer and specifically binding to a target analyte, (iii) a detection area made of a porous membrane including a test line where a second binder specifically binding to the target analyte bound with the first binder of the conjugate is immobilized and a control line where a third binder specifically binding to the first binder without specifically binding to the target analyte is immobilized, and (iv) an adsorption pad, which are disposed sequentially toward the other end from one end based on the length of the strip. Four regions constituting the immunodetection sensor based on lateral flow assay are typically stacked on a backing card or backing sheet by a plastic adhesive. In addition, the respective pads may be disposed to be in contact with each other or overlapped with each other, so that a sample solution may move along the immunodetection sensor based on lateral flow assay in the assay process. Typically, the width of the overlapped region may be, for example, in the range of about 1 to 3 mm, specifically about 1.5 to 2 mm, but the present invention is not limited thereto.

In an exemplary embodiment, the sample (or sample solution) passes through the conjugate pad via the sample pad and flows until reaching the test line and the control line through the membrane-type detection area. As such, the sample pad, the conjugate pad, the membrane-type detection area, and the adsorption pad all fluid-communicate with each other.

In an exemplary embodiment, the minimum amount of the target analyte in the sample (that is, detection limit; the minimum amount of the target analyte required in the sample or sample solution during detection) may be, for example, in the range of at least about 0.01 ng/ml, specifically at least about 0.1 ng/ml, more specifically at least about 1 ng/ml, but it is illustrative and can be changed according to a type, a characteristic, and the like of the target analyte.

Specifically, the sample pad typically performs a plurality of functions of uniformly distributing a sample (specifically, a liquid analysis sample) and also transmitting the sample to an adjacent conjugate pad. The sample is moved from the sample pad toward the absorption pad as indicated by the arrow by capillary. According to the exemplary embodiment, the sample pad may be impregnated with a composition including a buffer salt, a protein, a surfactant, and another liquid capable of adjusting the flow rate of the sample. Further, the pores of the sample pad may serve to filter residual components (e.g., red blood cells).

The conjugate pad may serve to store a conjugate for immunodetection including nanoparticles, a polymer conjugated to the nanoparticles and detectable, and a plurality of first binders conjugated to the surface of the polymer and specifically binding to a target analyte and maintain the conjugate to be functionally stable until the test is performed. Specifically, the conjugate is present in a dry state and then applied with fluidity as the sample (or sample solution) containing the target sample to be move to the detection area of the membrane material located downstream. To this end, for example, a conjugate buffer composition containing carbohydrates (e.g., sucrose) and a resolubilization agent may be used. In this case, when the conjugate particles are dried in the presence of sugars, the sugar molecules forms a layer around the particles to be stabilized. As the sample solution is introduced into the conjugate pad, the sugar molecules are quickly dissolved to carry the conjugated particles into the fluid flow.

In the exemplary embodiment, the conjugate pad includes a conjugate for immunodetection including nanoparticles, a polymer conjugated to the nanoparticles and including a plurality of enzymes, and a first binder conjugated to the surface of the polymer and specifically binding to a target analyte, and to this end, a method such as spray, impregnation, and the like may be used. At this time, the first binder may specifically (or optionally) bind to the target analyte, and such specific binding may involve complementary binding. That is, the first binder may bind (i.e., specifically bind) to only a specific target analyte, and may not bind to other molecules in the sample. Illustratively, the first binder may be an antibody (or antibody fragment), and the antibody may specifically (or optionally) bind to an antigen which is the target analyte. In the case of the gold nanoparticles conjugated to the first binder in the conjugate, a detectable characteristic is color, and may be, for example, orange, red, purple, etc.

In the exemplary embodiment, the conjugate (the conjugate of the first binder and the gold nanoparticles) binds to the target analyte in the sample (when the target analyte is present in the sample) to move to the detection area.

In the exemplary embodiment, the detection area is formed in a membrane, specifically a porous membrane shape, and for example, may be selected from cellulose, glass fiber, nitrocellulose, polyvinylidene fluoride, charge-modified nylon, polyether sulfone, and the like. More typically, nitrocellulose may be used. In the detection area, the test line and the control line are sequentially arranged in the flow direction of the sample, and illustratively, each of the test line and the control line may be formed in a line pattern extending across the membrane. In addition, the control line may be located downstream of the test line on the flow direction of the sample.

In the test line, a second binder that specifically binds to the target analyte binding to the first binder in the conjugate is immobilized. At this time, similarly to the first binder, the second binder may also specifically (or optionally) bind to the target analyte, and specifically, may capture the conjugate via the target analyte (when the target analyte is present in the sample) specifically binding to the first binder of the conjugate (sandwich type). In this regard, the second binder may be an antibody when the target analyte is an antigen.

In the exemplary embodiment, the conjugate moves toward the absorption pad in the detection area made of a porous material through the capillary phenomenon. At this time, the pore size of the membrane made of the porous material may be in the range of, for example, about 0.05 to 12 μm, specifically about 0.1 to 7 μm.

When the target analyte exists in the sample, a kind of conjugate (e.g., antigen-antibody-enzyme polymer-gold nanoparticle) is formed by specifically binding to the first binder binding to the conjugate. The conjugate formed as such is captured by the second binder (e.g., an antibody specifically binding to the target analyte) immobilized on the test line, and as a result, the gold nanoparticles are accumulated in the test line to express a specific color (positive test result). At this time, the size of the gold nanoparticle is designed to move through the pores in the detection area of the porous membrane. In addition, the gold nanoparticle may be easily bound or coated onto the first binder (e.g., antibody). As described above, when the gold nanoparticles are captured on the test line, the gold nanoparticles interact with visible light to cause a change (specifically, color) detectable visually or by various detection devices (or analysis devices). On the other hand, when the conjugate does not bind to the target analyte, the conjugate passes through the test line together with the flow of the sample.

Meanwhile, in the case of the control line of the detection area, the third binder that binds to the first binder without specifically binding to the target analyte may be immobilized. For example, the third binder may specifically bind to the first binder. In this regard, the first binder may be a primary antibody binding to the target analyte. Therefore, the conjugate may be captured on the control line by binding to the third binder, even if passing through the test line without binding to the target analyte. For example, when the target analyte is not present in the sample, a color and the like are expressed in the control line even if the color and the like are not expressed in the test line. As such, the response in the control line means that the liquid sample appropriately passes through the sensor (that is, a signal from the control line indicates that the conjugate is present and the third binder binds to the conjugate, the immunodetection sensor appropriately operates).

Specifically, the third binder binds to the first binder conjugated to the gold nanoparticle in the conjugate to be accumulated on the control line, regardless of the presence of the target analyte in the sample. According to the exemplary embodiment, the third binder may be a polyclonal antibody or a monoclonal antibody that exhibits specificity for antibody fragments such as an Fc region or an Fab region or the entire Ig molecule as a secondary antibody. For example, when a conjugate of a gold nanoparticle and mouse-anti human IgG is used as the conjugate, the third binder in the control line may be an anti-mouse IgG, for example, goat anti-mouse IgG antibody, and the like as the antibody.

As described above, a sample (or sample solution) through the control line is absorbed into the absorption pad which is in contact with the detection area made of the membrane while located downstream. The absorption pad is attached to an end of the strip-type immunodetection sensor based on lateral flow assay to absorb an excess reaction reagent, thereby preventing the backflow of the liquid and collect the treated liquid, and the absorption pad allows the use of a large volume of sample solution to increase the sensitivity of the test. In the exemplary embodiment, the absorption pad may be a material of a cellulose filter and the like.

In the immunodetection sensor according to the present invention, the nanoparticles may be gold nanoparticles, the polymer may be a polymer in which a plurality of horseradish peroxidases and streptavidin bind to a dextran polymer backbone, and the first binder may be an antibody conjugated with biotin, wherein the polymer and the first binder may bind to each other by a biotin-streptavidin bond.

In the immunodetection sensor according to the present invention, the nanoparticles may be gold nanoparticles, the polymer may be a polymer in which a plurality of alkaline phosphatases and streptavidin bind to a dextran polymer backbone, and the first binder may be an antibody conjugated with biotin, wherein the polymer and the first binder bind to each other by a biotin-streptavidin bond.

According to yet another exemplary embodiment of the present invention, there is provided an immunodetection method based on lateral flow assay comprising: mixing a sample with the conjugate for immunodetection based on lateral flow assay described above to specifically bind the conjugate to a target analyte in the sample.

According to yet another exemplary embodiment of the present invention, there is provided an immunodetection signal amplification method comprising: mixing a sample with the conjugate for immunodetection based on lateral flow assay described above to specifically bind the conjugate to a target analyte in the sample.

According to yet another exemplary embodiment of the present invention, there is provided a method for manufacturing any one conjugate for immunodetection based on lateral flow assay described above comprising: S1) conjugating nanoparticles and a polymer including a plurality of enzymes; and S2) conjugating a first binder specifically binding to a target analyte to the polymer in the nanoparticle-polymer conjugate.

The manufacturing method may further include immobilizing a blocker to a portion of the surface of the nanoparticle to which the polymer is not conjugated, after step S1).

In the method for manufacturing the conjugate for immunodetection of the present invention, since the conjugate is manufactured while conjugating the polymer to the nanoparticles, in the process of performing washing and purification, for example, the conjugate may be quickly and rapidly washed and purified using a centrifuge. Unlike this, when the conjugate is manufactured only by the enzyme polymer without nanoparticles, it takes a minimum of 12 hours because of a dialysis process required for washing and purification. Accordingly, the present invention may shorten the washing and purification times required for manufacturing the conjugate.

According to the manufacturing method of the conjugate for immunodetection of the present invention, after step S1), more specifically immobilizing the blocker, the method may further include a step of concentrating the conjugate before step S2). When the concentration process is performed, it is possible to increase a probability capable of reducing a distance between an AuNP-PolyEnzyme conjugate and an antibody.

In addition, the step S2) may be performed after replacing a buffer providing an optimum condition for performing the step S2) after the concentration step. For example, the obtained product of step S1) is centrifuged and concentrated, a supernatant is removed, and then an appropriate amount of 1×PBS (pH 7.4) is added to make an environment (pH, ion concentration) in which binding between biotin attached to the antibody and streptavidin of AuNP-PolyEnzyme may occur best, thereby enhancing the yield.

In the method for manufacturing the conjugate for immunodetection according to the present invention, the nanoparticles may be at least one selected from the group consisting of metal nanoparticles, quantum dot nanoparticles, magnetic nanoparticles, carbon nanoparticles, latex beads/fluorescent nanoparticles, and cellulose nanoparticles.

In the method for manufacturing the conjugate for immunodetection according to the present invention, a blocker may be immobilized to a portion of the surface of the nanoparticle to which the polymer is not conjugated, wherein the blocker may be at least one selected from bovine serum albumin, egg albumin, skim milk, casein, soybean-fish derived components, polyethylene glycol (PEG), and polyethylene oxide (PEO).

In the method for manufacturing the conjugate for immunodetection according to the present invention, the polymer may include a first binding substance, the first binder may include a second binding substance, and the first binder may be conjugated or bind to the polymer by inter-binding of the first binding substance and the second binding substance. Here, the relative terms such as first and second are for distinguishing one binding substance from the other binding substance, and do not represent any order between the first binding substance and the second binding substance.

In the method for manufacturing the conjugate for immunodetection according to the present invention, the first binding substance and the second bonding substance may be one or more selected from the group consisting of an antigen other than a target antigen-antibody pair, a complementary nucleotide chain pair, a pair of an aptamer and a target substance, a pair of peptides binding to each other, and a pair of avidin or streptavidin and biotin.

In the method for manufacturing the conjugate for immunodetection according to the present invention, the enzyme may be at least one selected from horseradish peroxidase, alkaline phosphatase, β-galactosidase, arthromyces ramosus peroxidase, β-lactamase, glucose-6-phosphate dehydrogenase, urease, uricase, superoxide dismutase, luciferase, pyruvate kinase, lactate dehydrogenase, galactose oxidase, acetylcholine-sterase, enterokinase, tyrosinase, and xanthine oxidase.

In the method for manufacturing the conjugate for immunodetection according to the present invention, the plurality of enzymes bind to the polymer backbone to enable a detection reaction with a plurality of substrates introduced into the space of the polymer, and has advantages of improving 1000 to 10000 times the detection sensitivity, adjusting a signal amplification reaction, and increasing a detectable range.

In the method for manufacturing the conjugate for immunodetection according to the present invention, the polymer backbone may be at least one selected from dextran, dextrin, poly(diallyl dimethyl ammonium chloride), poly(vinylamine) hydrochloride, poly(L-lysinehydrobromide), poly(allylamine), poly(acrylamine), poly(allylamine hydrochloride), poly(4-aminostyrene), poly(N-methylvinylamine), poly(ethylene glycol), poly(diallyldimethylammonium chloride), chitosan, polysialic acids, poly(2-ethyl 2-oxazoline), hyaluronic acid, and hydroxyethyl-starch.

In the method for manufacturing the conjugate for immunodetection according to the present invention, the first binder may be antibodies, antigens, nucleic acids, aptamers, haptens, antigen proteins, DNA, RNA, DNA-binding proteins, RNA-binding proteins or hormone-receptors.

In the method for manufacturing the conjugate for immunodetection according to the present invention, the target analyte may be at least one selected from the group consisting of autoantibodies, ligands, natural extracts, peptides, proteins, metal ions, synthetic drugs, natural drugs, metabolites, genomes, virus and products by virus, and bacteria and products by bacteria, and may be particularly proteins, more particularly troponin and interleukin.

In the method for manufacturing the conjugate for immunodetection according to the present invention, the nanoparticles may be gold nanoparticles, the polymer may be a polymer in which a plurality of horseradish peroxidases and streptavidin bind to a dextran polymer backbone, and the first binder may be an antibody conjugated with biotin, wherein the polymer and the first binder may bind to each other by a biotin-streptavidin bond.

Hereinafter, the present invention will be described in more detail with reference to Examples. However, these Examples are just intended to explain the present invention in more detail, and the scope of the present invention is not limited thereto.

EXAMPLE 1

Manufacture of Conjugate for Immunodetection of the Present Invention

The conjugate for the immunodetection of the present invention was prepared through the following steps.

1) 1 mL of gold nanoparticles of 1× concentration (1.40× $10^{12}$/mL) and 100 mL of a 0.1 M borate buffer (pH 8.5) were sequentially added in a 1.5 mL EP tube and vertex-mixed for 30 seconds and then spin-down for 10 seconds and purified at 25° C. for 10 minutes.

2) 1 mg/mL of an HRP polymer was added by 10 mL in the solution, vertex-mixed for 30 seconds and then spin-down for 10 seconds and reacted at 25° C. for 1 hour using a rotating stirrer (25 rpm).

3) For blocking, 5 mL of 1×PBS (pH 7.4) containing 20% (g/g) BSA was added, vertex-mixed for 30 seconds and then spin-down for 10 seconds and purified and reacted at 4° C. for 30 minutes.

4) Washing was performed using a centrifuge. At this time, 15 nm gold nanoparticles were centrifuged at 15,000 rpm and 10° C. for 25 minutes and then a supernatant was removed, 1 mL of a 10 mM borate buffer (pH 8.5) was added, and pellets at the bottom of the EP tube were well released and mixed, and then washed using a centrifuge again. This process was repeated three times.

5) When the last washing process was finished, the supernatant was removed and concentrated, and then 100 mL of 1×PBS (pH 7.4) was added to release the pellets well.

6) 10 mL of a 1 mg/mL antibody binding to biotin was added in the solution and vertex-mixed for 10 seconds, and then spin-down for 10 seconds and purified and reacted at 25° C. for 2 hours.

7) For blocking, 5 mL of 5 mg/mL biotin-BSA was added, and purified and reacted at 25° C. for 30 minutes.

8) Washing was performed using a centrifuge. At this time, 15 nm gold nanoparticles were centrifuged at 15,000 rpm and 10° C. for 25 minutes and then a supernatant was removed, 1 mL of a 10 mM borate buffer (pH 8.5) was added, and pellets at the bottom of the EP tube were well released and mixed, and then washed using a centrifuge again. This process was repeated three times.

9) When the last washing process was finished, the supernatant was removed and 50 mL of a conjugate storage buffer was added to release well and store the pellets. At this time, the concentration of the conjugate was defined as 20×. The AuNP-PolyAPStA-Ab conjugate of the present invention was also manufactured in the same manner. The AuNP-PolyStA-Ab conjugate was manufactured in the same manner as described above by omitting step 2).

EXAMPLE 2

Analysis Results of Conjugate for Immunodetection of the Present Invention

The absorption spectrum of the conjugate for immunodetection according to the present invention was measured through the following method.

The gold nanoparticles and each conjugate were diluted using a 10 mM borate buffer (pH 8.5) so that the concentration thereof became 0.5× (1 mL). For example, 25 mL of a 20× conjugate was mixed with 975 mL of a 10 mM borate buffer (pH 8.5) and diluted to become a 0.5× concentration (1 mL). The absorbance was measured in the range of 400 to 700 nm of each sample using a spectrophotometer. At this time, a 10 mM borate buffer (pH 8.5) used as a diluent was used as a reference and the measurement was performed at 25° C. In the range of 400 to 700 nm, the wavelength corresponding to the maximum absorbance of each sample was confirmed.

The results of measuring the absorption spectrum of the conjugate for immunodetection according to the present invention by the method were shown in FIGS. 3A and 3B. It was confirmed that as the conjugation proceeded, a localized surface plasmon resonance (LSPR) peak shift was generated as a long wavelength, so that the reaction was performed well by each step.

Figure 4:
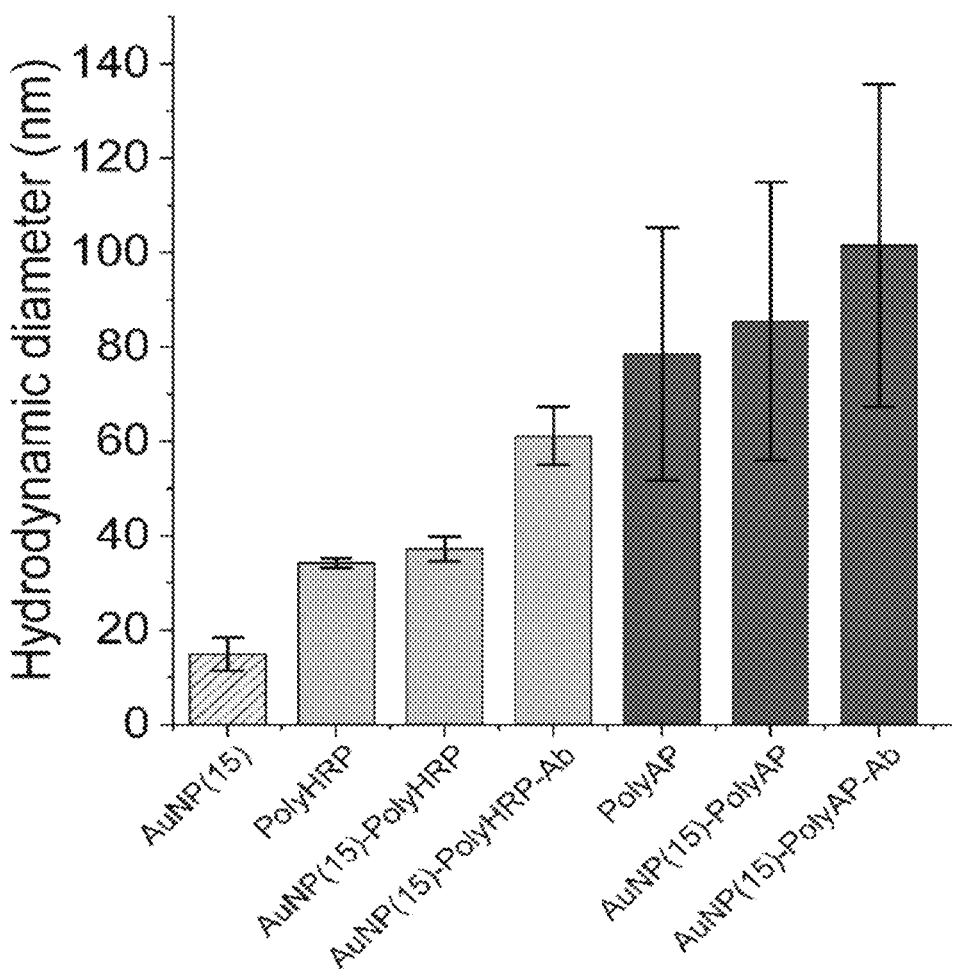
FIG. 4 is a diagram illustrating a size analysis result of the conjugate for immunodetection according to the exemplary embodiment of the present invention.

The size of the conjugate for immunodetection according to the present invention was measured using dynamic light scattering (DLS), and the results were shown in FIG. 4.

Through the DLS measurement, it was confirmed that the conjugate size was increased according to each step by measuring the PolyHRPStA size and the conjugate size, and it could be confirmed that the size by the adsorption reaction between AuNP and PolyHRPStA was increased and the conjugate size by a streptavidin-biotin bond of AuNP-PolyHRPStA and the antibody was increased. The increase in size of the AuNP-PolyAPStA-Ab conjugate of the present invention was also confirmed in the same manner.

EXAMPLE 3

Reaction Sensitivity of Conjugate for Immunodetection of the Present Invention Reaction Sensitivity Analysis of AuNP-Poly HRP Conjugate and AuNP-HRP Conjugate The HRP reaction sensitivity of the AuNP-PolyHRP conjugate was compared with the sensitivity of the HRP reaction of a single enzyme AuNP conjugate (AuNP-HRP) produced by adding PolyHRP and HRP in the same amount (based on protein concentration) at the same concentration.

As a result of the experiment, since HRP existed in the form linked to a polymer, the PolyHRP exhibited improved sensitivity due to an effect of adsorbing more HRPs than when the general HRP was adsorbed in a single AuNP (FIG. 5A). As a result, it could be seen that the sensitivity of the conjugate (AuNP-PolyHRP) using the enzyme polymer was better than the sensitivity of the conjugate (AuNP-HRP) using a single enzyme.

Reaction Sensitivity Analysis of AuNP-polyStA Conjugate and AuNP-StA Conjugate

It was confirmed that the conjugate for immunodetection of the present invention using PolyStA exhibited effects of increasing the intensity of a colorimetric (color) detection signal and improving the sensitivity. Results of detecting IL-8 in LFA using conjugates produced via StA (Streptavidin) and PolyStA (in the form in which a plurality of StAs were linked to one polymer), respectively, were compared. Since an antibody was labeled with biotin and at most 4 biotins may specifically bind to one StA, it was confirmed that in the case of using StA or PolyStA, the number of corresponding antibodies per AuNP may be increased as compared with the conjugate directly adsorbing the AuNP and the antibody (FIGS. 5B and 5C). When PolyStA according to the present invention was used as a conjugation medium, the signal intensity was significantly increased and the detection sensitivity was improved about 100 times with respect to the same concentration antigen as compared with a general AuNP-Ab conjugate. This indicates an additional 10-fold improved result from the result (about 10-fold improved detection sensitivity) when the antibody and AuNP were conjugated to each other using an StA single molecule as a conjugation medium. It was indicated that the number of antibodies corresponding to the AuNP may be dramatically improved by using a labeled (mediated) material polymer (PolyStA) to dramatically enhance the detection sensitivity in LFA (FIGS. 5B and 5C).

EXAMPLE 4

Room-temperature Storage of Conjugate for Immunodetection of the Present Invention The room-temperature stability of an AuNP-PolyHRP conjugate was evaluated through the following method.

1 μL of the conjugate during storing at room temperature was dropped to an NC membrane, and then dried at 37° C. for 15 minutes. A strip attached with a sample pad and an absorption pad was loaded with 90 μL of a luminol solution and after 5 minutes, a chemiluminescence signal was measured. The signal intensity measured at 1 day was set to 100% and compared with the measured signal to be converted to % value. A control group used an AuNP-HRP conjugate.

Figure 6:
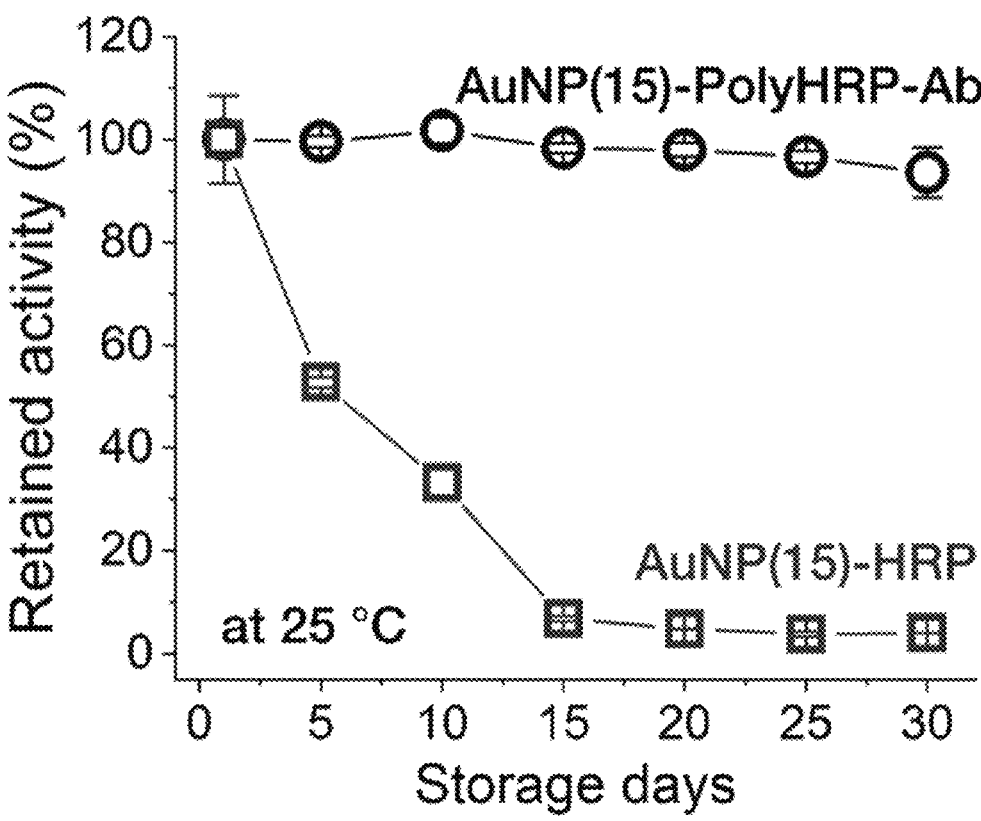
FIG. 6 is a diagram illustrating a result of evaluating the stability in room-temperature storage of the conjugate for immunodetection according to the exemplary embodiment of the present invention.

As the experimental results, it could be confirmed that the control AuNP-HRP conjugate was decreased in the stability as the storage period has elapsed, while the AuNP-PolyHRP conjugate was stable even in a long-term storage at room temperature (FIG. 6).

EXAMPLE 5

Reproducibility Verification of Conjugate for Immunodetection of the Present Invention In order to verify the reproducibility of the manufacture and the analysis result of the AuNP-PolyHRP-Ab conjugate of the present invention, verification was performed on three type batches.

Figure 7:
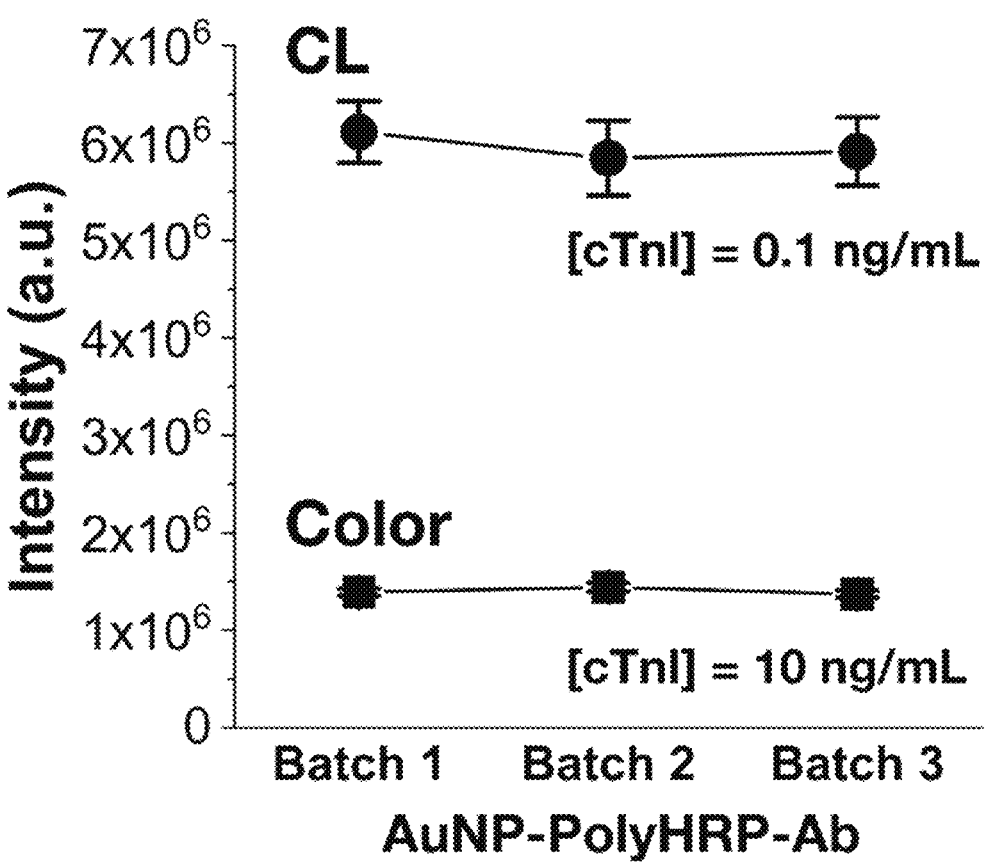
FIG. 7 is a diagram illustrating a result of verifying the reproducibility of the conjugate for immunodetection according to the exemplary embodiment of the present invention.
Figures 8A, 8B:
Figure 9B:
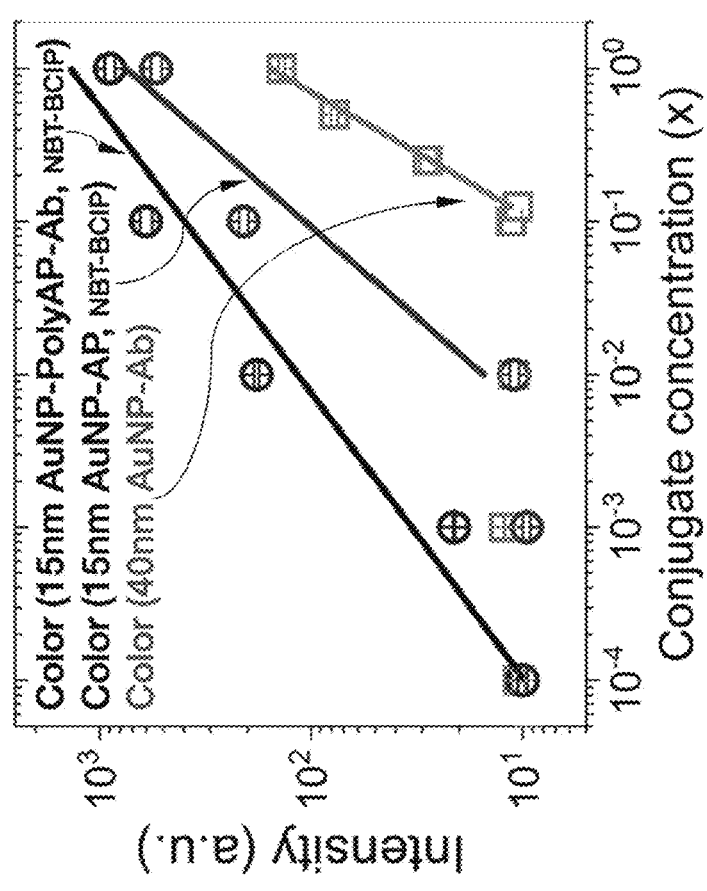
Figure 9A:
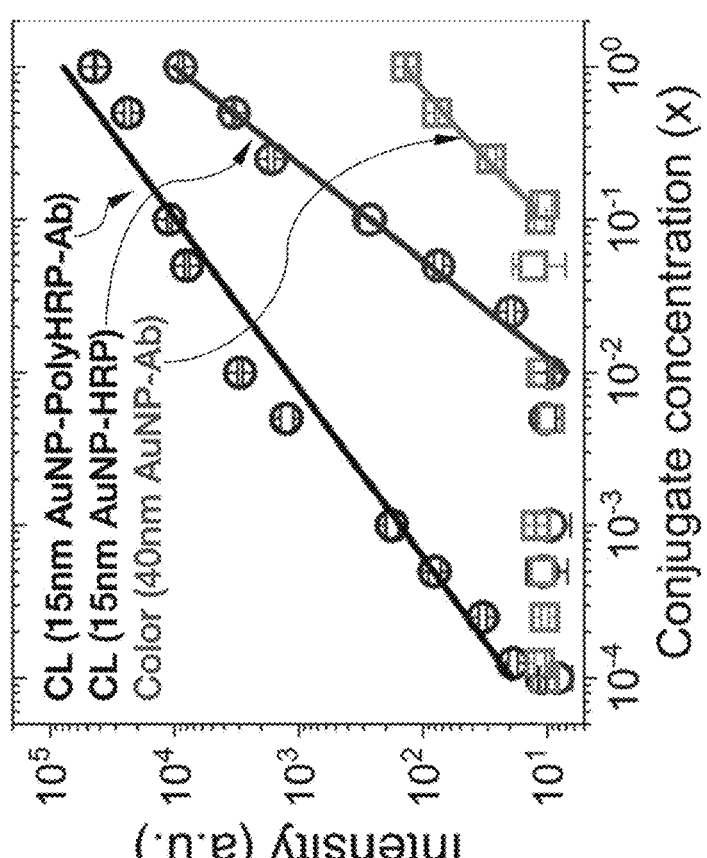
Figures 10A, 10B:
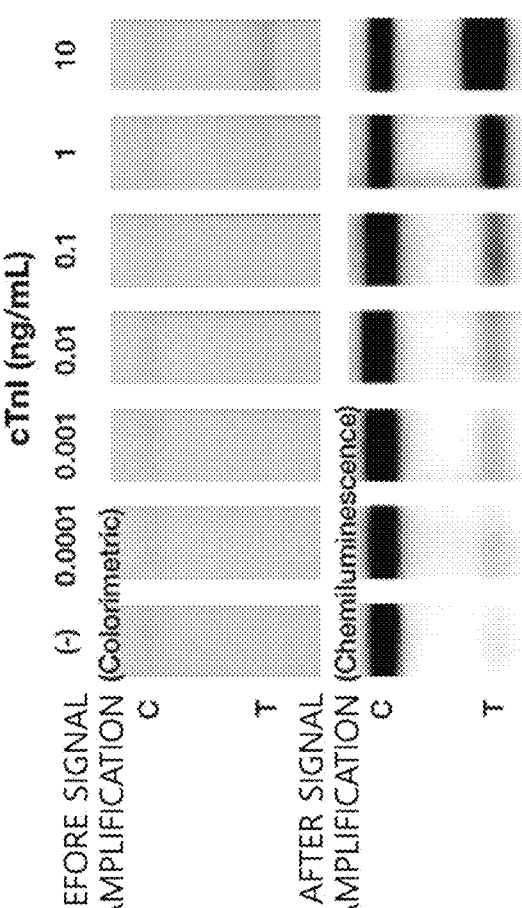
FIGS. 10A and 10B are diagrams illustrating a detection result of a conjugate (AuNPPolyHRPStA-Troponin I Antibody in a sensor) for immunodetection according to an exemplary embodiment of the present invention.

As a result of verification, excellent reproducibility was confirmed all in colorimetric (Color) method and a chemiluminescence (CL) method. In particular, the inter-batch coefficient of variation (CV, %) was confirmed to 2.67% and 2.32% in the Color and the CL, respectively (FIG. 7).

EXAMPLE 6

Performance Evaluation 1 of Conjugate for Immunodetection of the Present Invention When using a colorimetric method and a chemiluminescence method after spotting a solution diluted by the concentration of the conjugate on the membrane, it was confirmed which concentration signal detection was possible in each method. A detailed method was as follows.

1) After a conjugate was diluted sequentially to a concentration of 1× or less using a conjugate storage buffer as a diluent, the conjugate dilution solutions were dropped by 1 mL onto an NC membrane at 3.8 mm intervals combined with the absorption pad and the sample pad, and dried in a 37° C. oven for 15 minutes.

2) The colorimetric measurement was performed by dropping 100 mL of 1× PBS (pH 7.4) on the sample pad, and after 5 minutes and under a 0.12 sec exposure condition using a colorimetric mode of Chemidoc-MP image system (Bio-Rad, Hercules, CA, USA).

3) The chemiluminescence measurement was performed by dropping 100 mL of a luminal reaction solution (10 mM luminol, 5 mM 4-iodophenol, 1 mM $H_2O_2$ in 0.1M pH 8.5 Tris-HCl) on the sample pad, and after 5 minutes, under a 60 sec exposure condition using a chemiluminescence mode of Chemidoc-MP image system.

As the experimental result, it was confirmed that only to 0.25× can be detected by the colorimetric method (before signal amplification) of detecting the color intensity according to an AuNP amount in the conjugate, but up to 0.00025× can be detected by the chemiluminescence method (after signal amplification) of detecting the luminescence reaction generated using the enzyme in the conjugate (FIGS. 8A to 9B).

EXAMPLE 7

Performance Evaluation 2 of Conjugate for Immunodetection of the Present Invention The performance was evaluated by detecting cardiac troponin I (cTnI) and interleukin-8 (IL-8) using the conjugate for immunodetection of the present invention. A detailed method was as follows.

1) A membrane strip sensor used in this experiment consisted of a sample pad, a conjugate pad, an NC membrane, and an absorption pad. The sample pad was blocked with a 1 (g/g) casein solution, the conjugate pad was lyophilized with an AuNP-PolyHRPStA-TnI detection antibody conjugate, a test line of the NC membrane was immobilized with a TnI capture antibody (1 mg/mL, 1.19 mL/cm), and a control line was immobilized with an Anti-ms-IgG antibody (0.1 mg/mL, 1.00 mL/cm). The strip used in the IL-8 experiment was prepared in the same configuration as the strip used in the TnI experiment except for the detection/capture antibody. In the IL-8 experiment, an experiment using an AuNP-PolyHRPStA-IL-8 detection antibody conjugate (FIGS. 11A and 11B) and an experiment using an AuNP-PolyAPStA-IL-8 detection antibody conjugate (FIGS. 11C and 11D) were performed.

2) A cTnI or IL-8 antigen was spiked by concentration on the human serum just before the experiment, and during sample loading, was diluted to 1/10 with an analysis buffer and 100 mL was loaded on the sample pad.

3) After the reaction for 10 minutes, the washing process was performed for 5 minutes by adding 50 ml of 1×PBS (pH 7.4) to the sample pad.

4) The conjugate pad and the sample pad were removed from the strip sensor, 13 mL of a luminol reaction solution was loaded on the bottom of the NC membrane, and after 3 minutes, the signal was measured under a 60 sec exposure condition using a chemiluminescence mode of a Chemidoc-MP image system.

As the experiment result, it was confirmed that the conjugate of the present invention was used even at a very low level of antibody concentration to be effectively detected (FIGS. 10A to 11D).

EXAMPLE 8

Performance Evaluation 3 of Conjugate for Immunodetection of the Present Invention With respect to the conjugate for immunodetection of the present invention, after an antigen was detected by lateral flow assay, conjugate amounts remaining on the conjugate pad and the NC membrane were compared and the test spot signal intensity and the background signal intensity were analyzed to evaluate the performance of immunodetection. A detailed method was as follows.

1) A sample prepared to have the same PolyHRP and Ab amounts in a PolyHRP-Ab conjugate (control) and an AuNP-PolyHRP-Ab conjugate (Example) was treated on a conjugate pad (3.8>6 mm²) and dried at 37° C. for 30 minutes.

2) The conjugate pad was attached with the NC membrane treated with 0.9 μg cTnI Ab and 0.08 μg Anti-ms-IgG Ab together with the absorbing pad and the sample pad to fabricate an LFA strip.

3) 100 μl of a cTnI 0.1 ng/mL antigen solution was loaded on the sample pad of the strip and reacted for 15 minutes.

4) The strip after the reaction ended was dried at 37° C. for 15 minutes.

5) Even after the reaction, in order to compare the HRP amount remaining on the NC membrane and the conjugate pad, the dried strip was separated, a TMB solution was treated on the NC membrane and the conjugate pad by 20 μl and 10 respectively, and then reacted for 5 minutes, and the color change was confirmed.

6) The NC membrane was photographed in a colorimetric measurement mode of Chemi-Doc MP measurement equipment and the test spot and background intensities were analyzed.

As a result of comparing before and after a TMB coloring reaction of the conjugate pad (conj. pad), when the pad treated with Example (AuNP-PolyHRP-Ab conjugate) of the present invention was confirmed visually before and after the TMB coloring reaction, the color change slightly occurred, while in the pad treated with a control (PolyHRP-Ab conjugate), the color change very strongly occurred before and after the TMB coloring reaction. Through this, it was confirmed that in the LFA reaction process, the present invention has been easily released from the conjugate pad. On the other hand, it was confirmed that the control PolyHRP-Ab conjugate was not released from the conjugate pad and the remaining conjugate existed (the lower end of FIG. 12A). Thus, it can be seen that the efficiency of releasing the present invention (AuNP-PolyHRP-Ab conjugate) from the conjugate pad is very excellent as compared with the enzyme polymer-antibody conjugate.

In addition, through the comparison before and after the TMB coloring reaction of the NC membrane, the coloring degree at the test spot and the background portion was confirmed through the TMB reaction in the NC membrane, and through this, the degree of the immune response and the amount of HRP remaining in the background portion were compared. As the comparing result, in the NC membrane performing the immune response using Example (AuNP-PolyHRP-Ab conjugate) of the present invention, a color change of the background portion excluding the test spot and the control spot was not large even after the TMB coloring reaction. Thus, it can be confirmed that the AuNP-PolyHRP-Ab conjugate of the present invention passes through the NC membrane without almost non-specific reaction with NC membrane in the background portion other than the test spot and the control spot where the specific reaction occurs. On the other hand, in the NC membrane performing the immune reaction using the control (PolyHRP-Ab conjugate), a distinct color change occurred even in the background portion other than the test spot and the control spot after the TMB coloring reaction (the top of FIG. 12A). This is because the PolyHRP-Ab conjugate has not passed through the NC membrane and the remaining HRP reacted.

As a result, it was confirmed that the AuNP-PolyHRP-Ab conjugate of the present invention may pass through the NC membrane well to minimize a non-specific reaction, but the PolyHRP-Ab conjugate does not pass through the NC membrane well and the remaining amount is large to increase the background signal and cause the non-specific reaction.

Figures 12A, 12B:
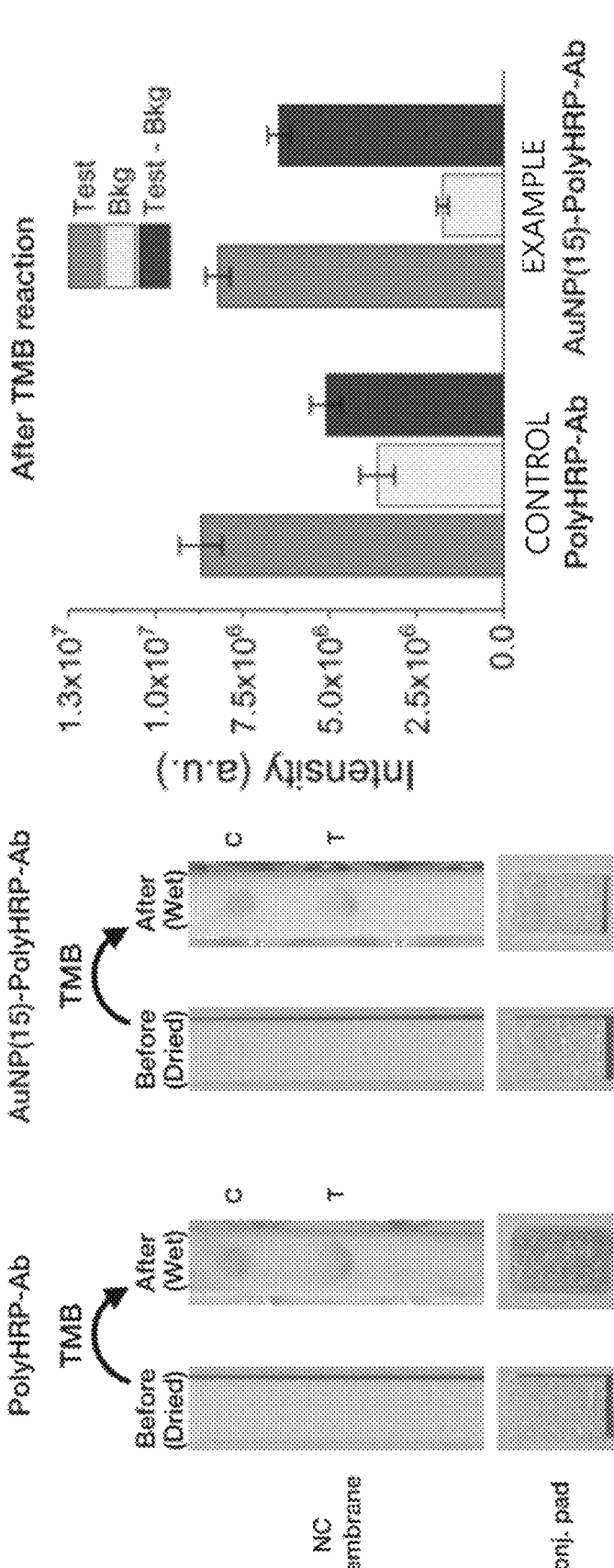
FIGS. 12A and 12B are diagrams illustrating a result of comparing TMB coloring reaction results to residual enzymes after immune response of the conjugate for immunodetection according to the exemplary embodiment of the present invention.

The results were illustrated in FIG. 12B as the result of numerically representing the signal intensities of the test spot and the background portion after the TMB reaction. In the case of the control (PolyHRP-Ab conjugate), it was confirmed that the signal intensities of the test spot and the background portion were entirely higher than Example (AuNP-PolyHRP-Ab conjugate) of the present invention. However, as a result of calculating the actual signal intensity (test spot signal intensity-background signal intensity) of the test spot removing the effect of the background signal, it was confirmed that the signal intensity of Example of the present invention is superior than the signal intensity of the control at the same antigen concentration (FIG. 12B).

Through the results, it can be seen that since the conjugate amount remaining on the background portion of the membrane and the conjugate pad after the LFA immunodetection reaction are minimum and the highest signal intensity is exhibited in the test spot or line after LFA immunodetection at the same concentration antigen as compared with the background signal, the conjugate of the present invention satisfied conditions of an excellent LFA conjugate for immunodetection.

Figure 13:
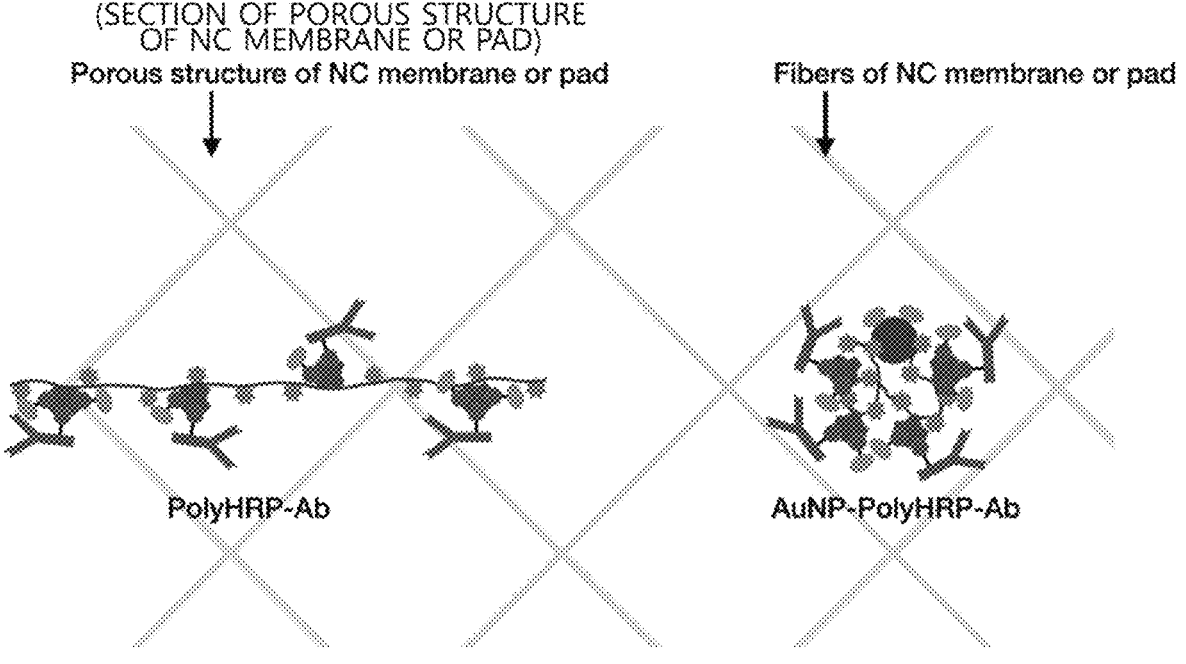
FIG. 13 is a theoretical schematic diagram of a principle of reducing a non-specific reaction and a background signal by the conjugate for immunodetection according to the exemplary embodiment of the present invention compared to a control group.

Specifically, the NC membrane used in the LFA or various pads are configured in a porous structure collecting fiber bundles and pores constituting the NC membrane or the pads, and when a liquid-state sample flows in the sample pad, this sample is moved along the pores by the capillary phenomenon, in the order of the sample pad, the conjugate pad, the NC membrane, and the absorption pad. At this time, in the case of the PolyHRP-Ab conjugate, due to an elongated linear polymer-shaped structure, the possibility to be captured in the fiber bundles or the pores of the membrane and the pad is increased, the resistance from the membrane or the pad is increased, and the passing efficiency of the PolyHRP-Ab conjugate in the membrane or the pad is reduced. As a result, even after washing due to the continuous flow of the sample solution, the conjugate remains on the membrane or pad to increase the possibility to cause a non-specific reaction or a high background signal. However, in the conjugate for immunodetection of the present invention, linear polymers are collected around a spherical structure of the nanoparticle to manufacture, for example, an AuNP-PolyHRP-Ab conjugate. Since the conjugate is formed in the form in which the polymers and antibodies are collected around the nanoparticles, the possibility to be captured in fiber bundles of the membrane and the pad is reduced to decrease the resistance from the membrane or the pad, so that the conjugate may pass through the pore (FIG. 13). Accordingly, the passing efficiency in the membrane or the pad of the conjugate for immunodetection of the present invention is improved, and in the case of the conjugate using the nanoparticles, the possibility that the conjugate may remain on the membrane and the pad is minimized by the washing process by the continuous flow of the sample solution to exhibit an effect of lowering the occurrence possibility of the non-specific reaction and the background signal.

As a result, through the experiments, the conjugate for immunodetection and the immunodetection method using the same according to the present invention, since it is possible to improve the detection sensitivity 1000 to 10000 times greater than a conventional antibody for immunodetection, to control whether to use a signal amplification reaction according to a concentration of an antibody to be detected, and to determine whether to detect the antigen, a detection dynamic range is increased and a process of manufacturing the conjugate is simplified and easy. Since the analysis is performed based on typical nanoparticles, the accuracy and reproducibility in the conjugate analysis and quantification process are excellent and enzymes in a polymer form are used to significantly increase the number of enzymes capable of being conjugated to individual nanoparticles, thereby enabling the ultra-high sensitive detection and enabling the detection to antigens at a low concentration within a relatively short time as compared with the related art. Since a ratio of binding to an enzyme polymer by binding of the enzyme polymer is higher than a ratio of directly attaching a binder (antibody) reacting with a target analyte to the nanoparticle surface, it is confirmed that the orientation is improved to have good reactivity to the target substance. Since the conjugate is manufactured around a spherical nanoparticle, it is confirmed that the resistance received from the membrane and the pad is lower than a polymer-antibody conjugate structure as a linear polymer structure to have excellent flow efficiency, so that accurate result signal detection is possible due to a low non-specific reaction and a background signal.

Hereinabove, while the preferred exemplary embodiments of the present invention have been described, it should be understood that these exemplary embodiments are just an exemplary embodiment for implementing the technical idea of the present invention and any modifications or changes for implementing the technical idea of the present invention cover the scope of the present invention.

The invention claimed is:

1. A conjugate for immunodetection based on lateral flow assay comprising:
   nanoparticles;
   a polymer conjugated to the nanoparticles,
   wherein the polymer includes a plurality of enzymes and streptavidin; and
   a first binder conjugated with biotin and specifically binding to a target analyte,
   wherein the first binder is conjugated to the surface of the polymer by a streptavidin-biotin bond.

2. The conjugate for immunodetection based on lateral flow assay of claim 1, wherein the nanoparticles are at least one selected from the group consisting of metal nanoparticles, quantum dot nanoparticles, magnetic nanoparticles, carbon nanoparticles, latex beads/fluorescent nanoparticles, and cellulose nanoparticles.

3. The conjugate for immunodetection based on lateral flow assay of claim 1, wherein a blocker is immobilized to a portion of the surface of the nanoparticle to which the polymer is not conjugated.

4. The conjugate for immunodetection based on lateral flow assay of claim 3, wherein the blocker is at least one selected from bovine serum albumin, egg albumin, skim milk, casein, soybean-fish derived components, polyethylene glycol (PEG), and polyethylene oxide (PEO).

5. The conjugate for immunodetection based on lateral flow assay of claim 1, wherein the enzyme is at least one selected from horseradish peroxidase, alkaline phosphatase, β-galactosidase, arthromyces ramosus peroxidase, β-lactamase, glucose-6-phosphate dehydrogenase, urease, uricase, superoxide dismutase, luciferase, pyruvate kinase, lactate dehydrogenase, galactose oxidase, acetylcholine-sterase, enterokinase, tyrosinase, and xanthine oxidase.

6. The conjugate for immunodetection based on lateral flow assay of claim 1, wherein the plurality of enzymes bind to a polymer backbone to enable a detection reaction with a plurality of substrates to be introduced into a space of the polymer.

7. The conjugate for immunodetection based on lateral flow assay of claim 6, wherein the polymer backbone is at least one selected from dextran, dextrin, poly(diallyl dimethyl ammonium chloride), poly(vinylamine) hydrochloride, poly(L-lysinehydrobromide), poly(allylamine), poly(acrylamine), poly(allylamine hydrochloride), poly(4-aminostyrene), poly(N-methylvinylamine), poly(ethylene glycol), poly(diallyldimethylammonium chloride), chitosan, polysialic acids, poly(2-ethyl 2-oxazoline), hyaluronic acid, and hydroxyethyl-starch.

8. The conjugate for immunodetection based on lateral flow assay of claim 1, wherein the first binder is antibodies, antigens, nucleic acids, aptamers, haptens, antigen proteins, DNA, RNA, DNA-binding proteins, RNA-binding proteins or hormone-receptors.

9. The conjugate for immunodetection based on lateral flow assay of claim 1, wherein the target analyte is at least one selected from the group consisting of autoantibodies, ligands, natural extracts, peptides, proteins, metal ions, synthetic drugs, natural drugs, metabolites, genomes, virus and products by virus, and bacteria and products by bacteria.

10. The conjugate for immunodetection based on lateral flow assay of claim 1, wherein the nanoparticles are gold nanoparticles, the polymer is a polymer in which a plurality of horseradish peroxidases and streptavidin bind to a dextran polymer backbone, and the first binder is an antibody conjugated with biotin, wherein the polymer and the first binder bind to each other by a biotin-streptavidin bond.

11. The conjugate for immunodetection based on lateral flow assay of claim 1, wherein the nanoparticles are gold nanoparticles, the polymer is a polymer in which a plurality of alkaline phosphatases and streptavidin bind to a dextran polymer backbone, and the first binder is an antibody conjugated with biotin, wherein the polymer and the first binder bind to each other by a biotin-streptavidin bond.

12. An immunodetection sensor based on lateral flow assay comprising the conjugate for immunodetection based on lateral flow assay according to claim 1.

13. An immunodetection sensor based on lateral flow assay comprising:
   (i) an absorptive sample pad;
   (ii) a conjugate pad including the conjugate for immunodetection based on lateral flow assay according to claim 1;
   (iii) a detection area made of a porous membrane including a test line where a second binder specifically binding to the target analyte bound with the first binder of the conjugate is immobilized and a control line where a third binder specifically binding to the first binder without specifically binding to the target analyte is immobilized; and
   (iv) an adsorption pad, which are disposed sequentially toward the other end from one end.

* * * * *